United States Patent
Bendikov et al.

(10) Patent No.: US 8,921,582 B2
(45) Date of Patent: Dec. 30, 2014

(54) OLIGO- AND POLYFURANS, PREPARATION AND USES THEREOF

(71) Applicants: Yeda Research and Development Co. Ltd., Rehovot (IL); Tatyana Bendikov, Rehovot (IL)

(72) Inventors: Michael Bendikov, Rehovot (IL); Ori Gidron, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/195,880

(22) Filed: Mar. 4, 2014

(65) Prior Publication Data
US 2014/0179934 A1 Jun. 26, 2014

Related U.S. Application Data

(62) Division of application No. 13/392,641, filed as application No. PCT/IL2010/000700 on Aug. 26, 2010, now Pat. No. 8,759,550.

(60) Provisional application No. 61/237,330, filed on Aug. 27, 2009.

(51) Int. Cl.
*C07D 407/14* (2006.01)
*C07D 307/34* (2006.01)

(52) U.S. Cl.
CPC ............ *C07D 407/14* (2013.01); *C07D 307/34* (2013.01)
USPC ........................................................ 549/472

(58) Field of Classification Search
USPC ........................................................ 549/472
See application file for complete search history.

(56) References Cited

U.S. PATENT DOCUMENTS

| | | | |
|---|---|---|---|
| 4,569,734 | A | 2/1986 | Naarmann et al. |
| 4,640,749 | A | 2/1987 | Naarmann et al. |
| 4,758,634 | A | 7/1988 | Jenekhe |
| 4,818,646 | A | 4/1989 | Takakubo et al. |
| 4,987,042 | A | 1/1991 | Jonas et al. |
| 5,108,573 | A | 4/1992 | Rubinstein et al. |
| 5,919,951 | A | 7/1999 | Chmii et al. |
| 6,184,540 | B1 | 2/2001 | Chmii et al. |

FOREIGN PATENT DOCUMENTS

| | | |
|---|---|---|
| CN | 101006592 A | 7/2007 |
| EP | 0880303 | 11/1998 |
| JP | H02-263824 A | 10/1990 |
| JP | 7 325329 | 12/1995 |
| JP | 2006-222251 A | 8/2006 |
| JP | S48-081893 A | 8/2006 |
| JP | 2007 012759 | 1/2007 |
| WO | WO 2005/005435 | 1/2005 |
| WO | WO 2005/014693 | 2/2005 |

OTHER PUBLICATIONS

Ishida et al., Novel Electron Acceptors Bearing a Heteroquinonoid System III: 2,5-Bis(dicyanomethylene)-2,5-dihydrofuran and Its Conjugated Homologues as Novel Oxygen-Containing Electron Acceptors, 1990, Bull. Chem. Soc. Jpn., 63, 2828-2835.*
Binder J. et al, "Simple Chemical Transformation of Lignocellulosic Biomass into Furans for Fuels and Chemicals", J. Am. Chem. Soc., 131(5), pp. 1979-1985, 2009.
Delaere D. et al. Influence of building block aromaticity in the determination of electronic properties of five-membered heterocyclic oligomers, Physical Chemistry Chemical Physics, 4(9), 1522-1530, 2002.
De Melo J. S. et al. "Comprehensive Investigation of the Photophysical Behavior of Oligopolyfurans" Journal of Physical Chemistry A, 104(30), pp. 6907-6911, 2000.
Fabian W.M.F, et al. "Computational methods as an aid in the design of fluorophores with predictable absorption and emission wavelengths" Journal of Luminescence, vol. 85, Issues 1-3, pp. 137-148, Dec. 1999.
Glenis S. et al. "Polyfuran: a new synthetic approach and electronic properties". J. Am. Chem. Soc. 1993, 115, 12519-12525.
Gonzalez-Tejera M.J. et al. "Polyfuran conducting polymers: Synthesis, properties, and applications" Synthetic Metals 158 (2008) 165-189.
Hutchison G.R. et al. "Electronic structure and band gaps in cationic heterocyclic oligomers. Multidimensional analysis of the interplay of heteroatoms, substituents, molecular length, and charge on redox and transparency characteristics". Journal of Physical Chemistry B. Mar. 3;109(8):3126-38, 2005.
International Search Report No. PCT/IL/2010/000700 Date of mailing Nov. 22, 201.
Ishida et al., Bull Chem Soc. Japan. vol. 63, 2828-2835 (1990). Novel electron acceptors bearing heteroquinonoid System III: 2,5-Bis (dicyanomethylene)-2,5-dihydrofuran and Its Conjugated Homologues as Novel Oxygen-containing Electron Acceptors.
Kauffman, J M. et al. "Novel Fluorescent Quarter and Quinquifurans: Syntheses and Photophysical Properties"Journal of Heterocyclic Chemistry, 39, 981-988 (2002).
Jones G., et al. "Solvent effects on emission yield and lifetime for coumarin laser dyes—requirement for a rotary decay mechanism", Journal Physical Chemistry, 89(2), pp. 294-300, 1985.
Miyata Y et al. Synthesis and Structural, Electronic, and Optical Properties of Oligo(thienylfuran)s in Comparison with Oligothiophenes and Oligofurans. Journal of Organic Chemistry, 70(4), pp. 1147-1153, 2005.
Vivas-Reyes, Ricardo et al. "Theoretical study to evaluate polyfuran electrical conductivity and the substituent effects on the polymeric chain" Revista Colombiana De Quimica, 37(1), 21-29, 2008.
Ye et al.; "The influence of electric field on the geometry, electronic structure and transport behavior of oligofurans", Journal of Atomic and Molecular Physics, vol. 2, No. 1, Feb. 29, 2008, pp. 6-12.

(Continued)

*Primary Examiner* — Kristin Vajda
(74) *Attorney, Agent, or Firm* — Pearl Cohen; Zedek Latzer Baratz LLP; Mark S. Cohen

(57) ABSTRACT

This invention is directed to oligofurans, process of preparation and uses thereof.

17 Claims, 16 Drawing Sheets

(56) References Cited

OTHER PUBLICATIONS

Office Action for corresponding Chinese Application No. 201080047116.0 dated Oct. 18, 2013.

Abo et al.; "Transition Metal-induced Activation of Alkynes Leading to Metal Carbene Species: Synthetic Application to New Π-Conjugated Molecules", Journal of Physics: Conference Series 106 (2008) 012004.

Aleman et al.; "Theoretical Investigation of the 3,4-Ethylenedioxythiophene Dimer and Unsubstituted Heterocyclic Derivatives", The Journal of Physical Chemistry A, 2004, 108(8), 1440-1447.

Aleman et al.; "Structural and electronic properties of 3,4-ethylenedioxythiophene, 3,4-ethylenedisulfanylfurane and thiophene oligomers: A theoretical investigation", Synthetic Metals, 2005, 149, 151-156.

Asgari et al.; "A Facile and Efficient Reaction of Aromatic Aldehydes with the Isocyanide-Dialkylacetylenedicarboxylate Zwitter Ions: Formation of 2-Amino-5-aryl Furan Derivatives", Asian Journal of Chemistry vol. 22, No. 5 (2010), 3435-3438.

Bew et al.; "Expedient Syntheses of β-Iodofurans by 5-endo-dig Cyclisations", European Journal of Organic Chemistry, 2007, (34), 5759-5770.

Hari et al.; "Facile One-Pot Synthesis of Di-and Tri-Substituted Furans from Acyl Isocyanates Using Trimethylsilyldiazomethane", Syntesis, 2004, (9), 1359-1362.

Ishida et al.; "2,5-bis(dicyanomethylene)-2,5-dihydrofuran and its conjugated homologues as novel oxygen-containing electron acceptors", 1991, 41(3), 811-814.

Ma et al.; "Facile Synthesis of Highly Substituted 3-Aminofurans from Thiazolium Salts, Aldehydes, and Dimethyl Acetylenedicarboxylate", The Journal of Organic Chemistry, 2005, 70(22), 8919-8923.

Nakatani et al.; "Novel synthesis of bifurans via furan-forming photocyclization of α-diketones conjugated with ene-yne", Tetrahedron Letters, 1997, 38(7), 1207-1210.

Office Action issued for Japanese Patent Application No. 2012-526181 on Jul. 8, 2014.

Peart et al.; "Macromolecules", Macromolecules, 2009, 42(13), 4449-4455.

Pennanen; "Studies on the Furan Series. Part VII. A Preparation of 2,3-Di(2-furyl and thienyl) furans", Journal of Heterocyclic Chemistry, 1977, 14(5), 745-748.

Prousek et al.; "Reactions and Spectral Properties of 2-Amino-3-Cyano-4,5- Disubstituted Furane Derivatives", Collection Czechoslov. Chem. Commun. [vol. 45] [1980], pp. 1581-1582.

Redman et al.; "Preparation of 5-Substituted 3-Aminofuran-2-carboxylate Esters", Organic Letters, 2000, 2(14), 2061-2063.

Semire et al.; "Structural and electronic properties of chloromethylfuran oligomers: Semiempirical and DFT study", Oriental Journal of Chemistry vol. 25(4), 841-846 (2009).

Yamashita et al.; "Synthesis of Cyclopent via Reaction of Furan Chromium Carbene Complexes with Alkynes", Tetrahedron Letters, 1988, 29(28), 3403-3406.

Yamashita et al.; "Reactions of alkylthio-substituted chromium carbene complexes with alkynes: application to synthesis of visnagan", The Journal of Organic Chemistry, 1989, 54(19), 4481-4483.

Yavari et al.; "A simple approach to the synthesis of dialkyl 5-tert-butylamino- [2,2]bifuranyl-3,4-dicarboxylates", Tetrahedron Letters, 2004, 45, 7099-7101.

Zhang et al.; "Highly Electron-Donating 3,3'-Diaryl-1,1'-bi(isobenzofuran)s Synthesized by Photochemical Exocyclic [2 +2 +2] Cycloaddition", Organic Letters, 2008, 10(16), 3591-3594.

\* cited by examiner

A

B

OLIGO- AND POLYFURANS, PREPARATION AND USES THEREOF

CROSS REFERENCE TO RELATED APPLICATIONS

This application is a Divisional application from U.S. application Ser. No. 13/392,641 filed May 2, 2012 which is a National Phase Application of PCT International Application No. PCT/IL2010/000700, International Filing Date Aug. 26, 2010, claiming priority of U.S. Patent Applications, 61/237, 330, filed Aug. 27, 2009, which are all incorporated in their entirety herein by reference

FIELD OF THE INVENTION

This invention is directed to oligofurans, process of preparation and uses thereof.

BACKGROUND OF THE INVENTION

Organic molecules with long π-conjugation have received much attention as advanced materials and as the building blocks of nano-scale devices for use in solar cells, organic light emitting diodes (OLEDs), organic field effect transistors (OFETs), organic light emitting transistors (OLETs), batteries, electro-luminescent material and sensors. Stability, good solid state packing, processability, rigidity/planarity, high fluorescence, and a HOMO-LUMO gap in the semiconductor region (which also leads to absorption/emission in the visible range) are among the main requirements for useful advanced organic electronic materials to be applied as functional materials in organic electronic nano-technologies. Those materials are also used for various industrial applications such as antistatic coatings, dyes or pigments.

The conjugated chains and the electrical and optical properties of these polymers are influenced by the electronegativity of the heteroatom.

The synthesis of polyfuran by electrochemical means requires high voltage for the electropolymerization (1.8-2.5V) which results in irreversible oxidation of the polymer. Electropolymerization process, using terfuran provides milder polymerization due to its lower oxidation potential compared to furan.

Chemical polymerization of furan using a number of oxidizing agents using oxygen and a Ni catalyst, ferric chloride, and potassium ferricyanide resulted in only -polymers of poor quality resulting in low conjugation length. Another oxidizing agent which was used is pyridinium chlorochromate (PCC) resulting also in poor quality polymers.

Accordingly, it is an object of the present application to provide high quality and stable oligofurans and polyfurans.

SUMMARY OF THE INVENTION

In one embodiment, this invention provides an oligofuran represented by the structure of formula IV:

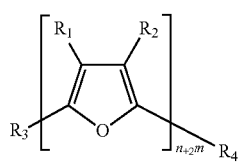

wherein
$R_1$, $R_2$, $R_3$ and $R_4$ are independently hydrogen, $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocycloalkyl, ($C_0$-$C_{18}$ alkyl)-aryl, ($C_0$-$C_{18}$ alkyl)-heteroaryl, CN, $CO_2$H, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)($C_1$-$C_{18}$ alkyl)], halo-($C_1$-$C_{18}$ alkyl), hydroxyl-($C_1$-$C_{18}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2$H, OH, SH, $NH_2$, $CO_2$—($C_1$-$C_6$ alkyl), O—($C_1$-$C_6$alkyl), S—($C_1$-$C_6$ alkyl), NH($C_1$-$C_6$ alkyl), NHC(O)($C_1$-$C_6$alkyl) or N[($C_1$-$C_6$ alkyl)][C(O)($C_1$-$C_6$ alkyl)];

or $R_1$ and $R_2$ combine to form a 4-8 membered ring comprising 0-3 double bonds and 0-3 heteroatoms selected from O, N, Se or S wherein said 4-8 membered ring is optionally substituted with 1-3 groups comprising $C_1$-$C_{18}$-alkyl, ($C_0$-$C_6$ alkyl)-cycloalkyl, ($C_0$-$C_6$ alkyl)-aryl, ($C_0$-$C_6$ alkyl)-heteroaryl, CN, $CO_2$H, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), dialkylamine, NHC(O)($C_1$-$C_6$ alkyl) or N[($C_1$-$C_6$ alkyl)] [C(O)($C_1$-$C_6$ alkyl)]; wherein said aryl, cycloalkyl and heteroaryl groups of said ($C_0$-$C_6$ alkyl)-aryl, ($C_0$-$C_6$ alkyl)-cycloalkyl and ($C_0$-$C_6$ alkyl)-heteroaryl groups are optionally substituted with 1-3 groups comprising halide, $C_1$-$C_6$ alkyl, CN, $CO_2$H, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), N($R_4$)($R_5$), NHC(O)($C_1$-$C_6$ alkyl) or N[($C_1$-$C_6$ alkyl)][C(O)($C_1$-$C_6$ alkyl)];

m is an integer between 1-50; and n is an integer between 1-50; wherein if $R_1$ and $R_2$ are hydrogens then [n+2m] is not 3 or 4.

In one embodiment, this invention provides a process for the preparation of oligofuran of formula III(n+2m) comprising reacting a compound represented by the structure of formula I:

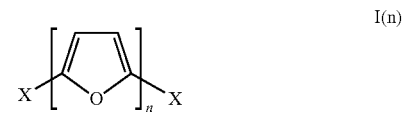

with 2-(tributyltin)-oligofuran of formula II:

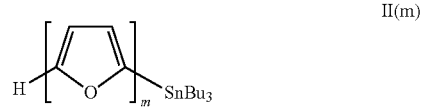

to yield oligofuran of formula III(n+2m):

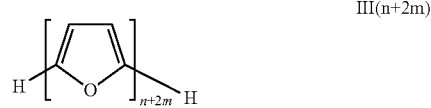

wherein X is Br or I;

n is an integer between 1-20; and m is an integer between 1-20.

In one embodiment, this invention provides an oligofuran of formula III(n+2m) prepared by the process described herein above.

In one embodiment, this invention provides an oligofuran represented by the structure of formula XIII:

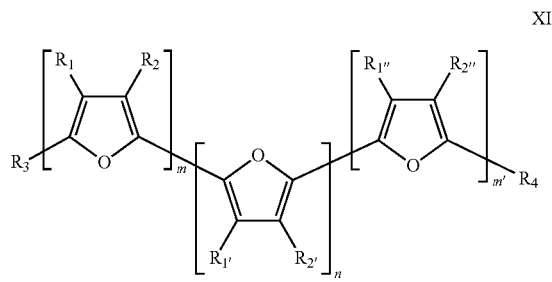

XIII wherein
$R_1, R_1', R_1'', R_2, R_2', R_2'', R_3$ and $R_4$ are independently hydrogen, $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocycloalkyl, ($C_0$-$C_{18}$ alkyl)-aryl, ($C_0$-$C_{18}$ alkyl)-heteroaryl, CN, $CO_2H$, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)($C_1$-$C_{18}$ alkyl)], halo-($C_1$-$C_{18}$ alkyl), hydroxyl -($C_1$-$C_{18}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), NHC(O)($C_1$-$C_6$ alkyl) or N[($C_1$-$C_6$ alkyl)][C(O)($C_1$-$C_6$ alkyl)];
or
$R_1$ and $R_2$; $R_1'$ and $R_2'$; $R_1''$ and $R_2''$ combine to form a 4-8 membered ring comprising 0-3 double bonds and 0-3 heteroatoms selected from O, N, Se or S wherein said 4-8 membered ring is optionally substituted with 1-3 groups comprising $C_1$-$C_{18}$-alkyl, ($C_0$-$C_6$ alkyl)-cycloalkyl, ($C_0$-$C_6$ alkyl)-aryl, ($C_0$-$C_6$ alkyl)-heteroaryl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), dialkylamine, NHC(O)($C_1$-$C_6$ alkyl) or N[($C_1$-$C_6$ alkyl)][C(O)($C_1$-$C_6$ alkyl)]; wherein said aryl, cycloalkyl and heteroaryl groups of said ($C_0$-$C_6$ alkyl)-aryl, ($C_0$-$C_6$ alkyl)-cycloalkyl and ($C_0$-$C_6$ alkyl)-heteroaryl groups are optionally substituted with 1-3 groups comprising halide, $C_1$-$C_6$ alkyl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), N($R_4$)($R_5$), NHC(O)($C_1$-$C_6$ alkyl) or N[($C_1$-$C_6$ alkyl)][C(O)($C_1$-$C_6$ alkyl)];
m is an integer between 1-50;
m' is an integer between 0-50 and
n is an integer between 1-50;
wherein if $R_1$, $R_1'$, $R_1''$ and $R_2$, $R_2'$, $R_2''$ are hydrogens then [n+m+m'] is not 3 or 4.

In one embodiment, the oligofurans of this invention are fluorescent.

In one embodiment, this invention provides a fluorescent marker comprising the oligofurans of this invention. In one embodiment, this invention provides a field effect transistor device comprising the oligofurans of this invention. In one embodiment, this invention provides a light emitting transistor device comprising the oligofurans of this invention.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
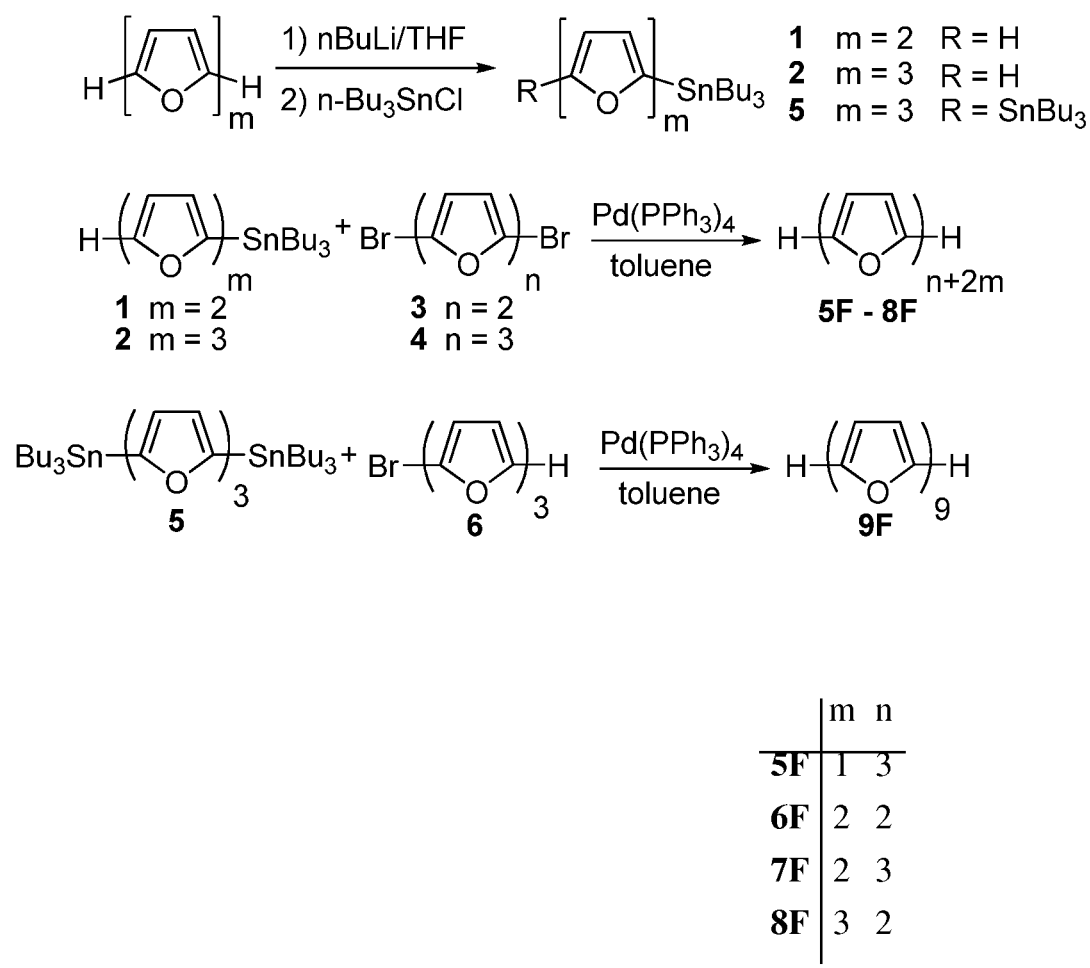
FIG. 1 depicts a synthetic scheme for the preparation of oligofurans of this invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention is directed to the synthesis and characterization of a series of stable α-oligofurans, which are highly fluorescent (compared to oligothiophenes and alternating furan-thiophene oligomers), electron rich, and exhibit tighter herringbone solid state packing, greater rigidity, and greater solubility than oligothiophenes.

In one embodiment, this invention provides an oligofuran represented by the structure of formula III:

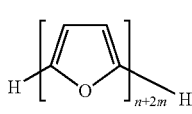

III(n+2m)

wherein m is an integer between 1-20; and
n is an integer between 1-20, wherein [n+2m] is not 3, or 4.

In another embodiment, [n+2m] of the oligomer of formula III is 5. In another embodiment, [n+2m] of the oligomer of formula III is 6. In another embodiment, [n+2m] of the oligomer of formula III is 7. In another embodiment, [n+2m] of the oligomer of formula III is 8. In another embodiment, [n+2m] of the oligomer of formula III is 9. In another embodiment, [n+2m] of the oligomer of formula III is 10. In another embodiment, [n+2m] of the oligomer of formula III is between 5-10. In another embodiment, [n+2m] of the oligomer of formula III is between 5-15. In another embodiment, [n+2m] of the oligomer of formula III is between 5-20. In another embodiment, [n+2m] of the oligomer of formula III is between 5-30. In another embodiment, [n+2m] of the oligomer of formula III is between 11-15. In another embodiment, [n+2m] of the oligomer of formula III is between 15-20. In another embodiment, [n+2m] of the oligomer of formula III is between 20-25. In another embodiment, [n+2m] of the oligomer of formula III is between 25-30. In another embodiment, [n+2m] of the oligomer of formula III is between 30-35. In another embodiment, [n+2m] of the oligomer of formula III is between 35-40. In another embodiment, [n+2m] of the oligomer of formula III is between 40-45. In another embodiment, [n+2m] of the oligomer of formula III is between 45-50. In another embodiment, [n+2m] of the oligomer of formula III is between 50-55. In another embodiment, [n+2m] of the oligomer of formula III is between 55-60. In another embodiment, [n+2m] of the oligomer of formula III is between 30-60.

In another embodiment, [n] of the oligomer of formula III is 1. In another embodiment, [n] of the oligomer of formula III is 2. In another embodiment, [n] of the oligomer of formula III is 3. In another embodiment, [n] of the oligomer of formula III is 4. In another embodiment, [n] of the oligomer of formula III is an integer between 3-5. In another embodiment, [n] of the oligomer of formula III is an integer between 3-8. In another embodiment, [n] of the oligomer of formula III is an integer between 5-10. In another embodiment, [n] of the oligomer of formula III is an integer between 10-20. In another embodiment, [n] of the oligomer of formula III is an integer between 15-20.

In another embodiment, [m] of the oligomer of formula III is 1. In another embodiment, [m] of the oligomer of formula III is 2. In another embodiment, [m] of the oligomer of formula III is 3. In another embodiment, [m] of the oligomer of formula III is 4. In another embodiment, [m] of the oligomer of formula III is an integer between 3-5. In another embodiment, [m] of the oligomer of formula III is an integer between 3-8. In another embodiment, [m] of the oligomer of formula III is an integer between 5-10. In another embodiment, [m] of the oligomer of formula III is an integer between 10-20. In another embodiment, [m] of the oligomer of formula III is an integer between 15-20.

In another embodiment, [m] of the oligomer of formula III is 2 and [n] is 1. In another embodiment, [m] of the oligomer of formula III is and [n] is 2. In another embodiment, [m] of the oligomer of formula III is 2 and [n] is 3. In another embodiment, [m] of the oligomer of formula III is 3 and [n] is 2. In another embodiment, [m] of the oligomer of formula III is 3 and [n] is 3.

In one embodiment, this invention provides an oligofuran represented by the structure of formula IV:

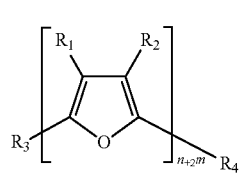

IV wherein
$R_1$, $R_2$, $R_3$ and $R_4$ are independently hydrogen, $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocycloalkyl, ($C_0$-$C_{18}$ alkyl)-aryl, ($C_0$-$C_{18}$ alkyl)-heteroaryl, CN, $CO_2H$, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)($C_1$-$C_{18}$ alkyl)], halo-($C_1$-$C_{18}$ alkyl), hydroxyl-($C_1$-$C_{18}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), NHC(O)($C_1$-$C_6$ alkyl) or N[($C_1$-$C_6$ alkyl)][C(O)($C_1$-$C_6$ alkyl)];
or
$R_1$ and $R_2$ combine to form a 4-8 membered ring comprising 0-3 double bonds and 0-3 heteroatoms selected from O, N, Se or S wherein said 4-8 membered ring is optionally substituted with 1-3 groups comprising $C_1$-$C_{18}$-alkyl, ($C_0$-$C_6$ alkyl)-cycloalkyl, ($C_0$-$C_6$ alkyl)-aryl, ($C_0$-$C_6$ alkyl)-heteroaryl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), dialkylamine, NHC(O)($C_1$-$C_6$ alkyl) or N[($C_1$-$C_6$ alkyl)][C(O)($C_1$-$C_6$ alkyl)]; wherein said aryl, cycloalkyl and heteroaryl groups of said ($C_0$-$C_6$ alkyl)-aryl, ($C_0$-$C_6$ alkyl)-cycloalkyl and ($C_0$-$C_6$ alkyl)-heteroaryl groups are optionally substituted with 1-3 groups comprising halide, $C_1$-$C_6$ alkyl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), N($R_4$)($R_5$), NHC(O)($C_1$-$C_6$ alkyl) or N[($C_1$-$C_6$ alkyl)][C(O)($C_1$-$C_6$ alkyl)];
m is an integer between 1-50; and
n is an integer between 1-50;
wherein if $R_1$ and $R_2$ are hydrogens then [n+2m] is not 3 or 4.

In one embodiment, $R_1$ and $R_2$ of the oligomer of formula IV are the same. In another embodiment $R_1$ and $R_2$ of the oligomer of formula IV are different. In another embodiment R1 of formula IV is hydrogen. In another embodiment $R_2$ of formula IV is hydrogen. In another embodiment $R_1$ and $R_2$ of formula IV are hydrogens. In another embodiment $R_1$ and $R_2$ are not hydrogens. In another embodiment $R_1$ of formula IV is an alkyl. In another embodiment $R_2$ of formula IV is an alkyl. In another embodiment $R_1$ and $R_2$ are an alkyl. In another embodiment $R_1$ and $R_2$ of formula IV are independently hydroxyalkyl. In another embodiment $R_1$ and $R_2$ of formula IV are independently halo-alkyl. In another embodiment $R_1$ and $R_2$ of formula IV are independently alkyl-aryl. In another embodiment $R_1$ and $R_2$ of formula IV are independently alkyl-aryl, wherein the aryl is substituted by an halogen. In another embodiment R₁ and R₂ of formula IV are independently alkyl-aryl, wherein the aryl is substituted by between 1-5 fluoro groups. In another embodiment R₁ and R₂ of formula IV are independently cycloalkyl, hetrocycloalkyl, aryl, or heteroaryl;

In one embodiment, R₁ and R₂ form together a 6 membered cycloalkyl ring. In one embodiment, R₁ and R₂ form together a 6 membered heterocyclic ring. In one embodiment, R₁ and R₂ form together a 6 membered aryl ring. In one embodiment, R₁ and R₂ form together a 6 membered heteroaryl ring. In one embodiment, R₁ and R₂ form together a 5 membered cycloalkyl ring. In one embodiment, R₁ and R₂ form together a 5 membered heterocyclic ring. In one embodiment, R₁ and R₂ form together a 5 membered aryl ring. In one embodiment, R₁ and R₂ form together a 5 membered heteroaryl ring.

In one embodiment, R₃ and R₄ of the oligomer of formula IV are the same. In another embodiment R₃ and R₄ of the oligomer of formula IV are different. In another embodiment R₃ of formula IV is hydrogen. In another embodiment R₄ of formula IV is hydrogen. In another embodiment R₃ and R₄ of formula IV are hydrogens. In another embodiment R₃ and R₄ are not hydrogens. In another embodiment R₃ of formula IV is an alkyl. In another embodiment R₄ of formula IV is an alkyl. In another embodiment R₃ and R₄ are an alkyl. In another embodiment R₃ and R₄ are hexyl. In another embodiment R₃ and R₄ are methyl. In another embodiment R₃ and R₄ are ethyl-hexyl. In another embodiment R₃ and R₄ are O-alkyl. In another embodiment R₃ and R₄ are methoxy group. In another embodiment R₃ and R₃ are alkyl-phenyl. In another embodiment R₃ and R₄ are alkyl-pentafluorophenyl. In another embodiment R₃ and R₄ are alkyl-fluorophenyl. In another embodiment R₃ and R₄ of formula IV are independently hydroxyalkyl. In another embodiment R₃ and R₄ of formula IV are independently halo-alkyl. In another embodiment R₃ and R₄ of formula IV are independently alkyl-aryl. In another embodiment R₃ and R₄ of formula IV are independently cycloalkyl, hetrocycloalkyl, aryl, or heteroaryl.

In another embodiment, [n+2m] of the oligomer of formula IV is 5. In another embodiment, [n+2m] of the oligomer of formula IV is 6. In another embodiment, [n+2m] of the oligomer of formula IV is 7. In another embodiment, [n+2m] of the oligomer of formula IV is 8. In another embodiment, [n+2m] of the oligomer of formula IV is 9. In another embodiment, [n+2m] of the oligomer of formula IV is 10. In another embodiment, [n+2m] of the oligomer of formula III is between 5-10. In another embodiment, [n+2m] of the oligomer of formula III is between 5-15. In another embodiment, [n+2m] of the oligomer of formula III is between 5-20. In another embodiment, [n+2m] of the oligomer of formula III is between 5-30. In another embodiment, [n+2m] of the oligomer of formula IV is between 11-15. In another embodiment, [n+2m] of the oligomer of formula IV is between 15-20. In another embodiment, [n+2m] of the oligomer of formula IV is between 20-25. In another embodiment, [n+2m] of the oligomer of formula IV is between 25-40. In another embodiment, [n+2m] of the oligomer of formula IV is between 40-60. In another embodiment, [n+2m] of the oligomer of formula IV is between 60-80. In another embodiment, [n+2m] of the oligomer of formula IV is between 80-100. In another embodiment, [n+2m] of the oligomer of formula IV is between 100-120. In another embodiment, [n+2m] of the oligomer of formula IV is between 120-130. In another embodiment, [n+2m] of the oligomer of formula IV is between 130-140. In another embodiment, [n+2m] of the oligomer of formula IV is between 140-150.

In another embodiment, [n] of the oligomer of formula IV is 1. In another embodiment, [n] of the oligomer of formula IV is 2. In another embodiment, [n] of the oligomer of formula IV is 3. In another embodiment, [n] of the oligomer of formula IV is 4. In another embodiment, [n] of the oligomer of formula IV is an integer between 3-5. In another embodiment, [n] of the oligomer of formula IV is an integer between 3-8. In another embodiment, [n] of the oligomer of formula IV is an integer between 5-10. In another embodiment, [n] of the oligomer of formula IV is an integer between 10-20. In another embodiment, [n] of the oligomer of formula IV is an integer between 15-20. In another embodiment, [n] of the oligomer of formula IV is an integer between 20-25. In another embodiment, [n] of the oligomer of formula IV is an integer between 25-30. In another embodiment, [n] of the oligomer of formula IV is an integer between 30-35. In another embodiment, [n] of the oligomer of formula IV is an integer between 35-50. In another embodiment, [n] of the oligomer of formula IV is an integer between 25-50.

In another embodiment, [m] of the oligomer of formula IV is 1. In another embodiment, [m] of the oligomer of formula IV is 2. In another embodiment, [m] of the oligomer of formula IV is 3. In another embodiment, [m] of the oligomer of formula IV is 4. In another embodiment, [m] of the oligomer of formula IV is an integer between 3-5. In another embodiment, [m] of the oligomer of formula IV is an integer between 3-8. In another embodiment, [m] of the oligomer of formula IV is an integer between 5-10. In another embodiment, [m] of the oligomer of formula IV is an integer between 10-20. In another embodiment, [m] of the oligomer of formula IV is an integer between 15-20. In another embodiment, [m] of the oligomer of formula IV is an integer between 20-25. In another embodiment, [m] of the oligomer of formula IV is an integer between 25-30. In another embodiment, [m] of the oligomer of formula IV is an integer between 30-35. In another embodiment, [m] of the oligomer of formula IV is an integer between 35-50. In another embodiment, [m] of the oligomer of formula IV is an integer between 25-50.

In another embodiment, [m] of the oligomer of formula IV is 2 and [n] is 1. In another embodiment, [m] of the oligomer of formula IV is and [n] is 2. In another embodiment, [m] of the oligomer of formula IV is 2 and [n] is 3. In another embodiment, [m] of the oligomer of formula IV is 3 and [n] is 2. In another embodiment, [m] of the oligomer of formula IV is 3 and [n] is 3.

In one embodiment, this invention is directed to an oligofuran represented by the structure of 5F:

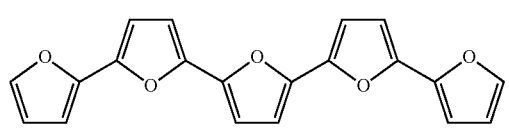

5F

In one embodiment, this invention is directed to an oligofuran represented by the structure of 6F:

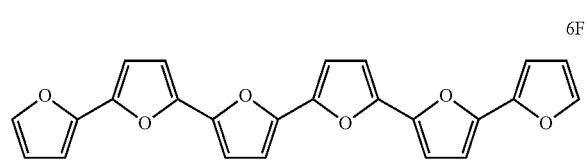 [SMILES: c1coc(-c2ccc(-c3ccc(-c4ccc(-c5ccc(-c6ccco6)o5)o4)o3)o2)c1]

6F

In one embodiment, this invention is directed to an oligofuran represented by the structure of 7F:

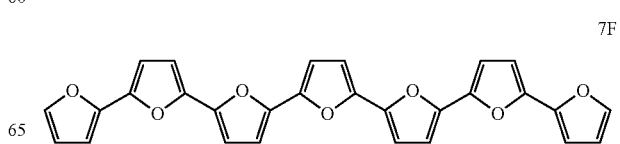

7F

In one embodiment, this invention is directed to an oligofuran represented by the structure of 8F:

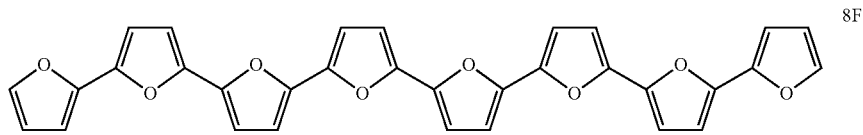 [SMILES: c1coc(-c2ccc(-c3ccc(-c4ccc(-c5ccc(-c6ccc(-c7ccc(-c8ccco8)o7)o6)o5)o4)o3)o2)c1]

8F

In one embodiment, this invention is directed to an oligofuran represented by the structure of 9F:

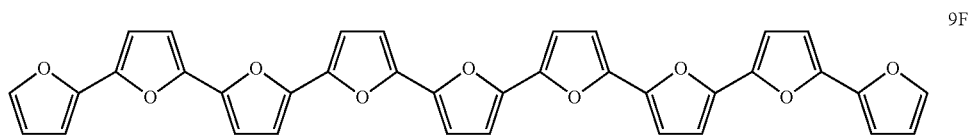 [SMILES: c1coc(-c2ccc(-c3ccc(-c4ccc(-c5ccc(-c6ccc(-c7ccc(-c8ccc(-c9ccco9)o8)o7)o6)o5)o4)o3)o2)c1]

9F

In one embodiment, this invention is directed to an oligofuran represented by the structure of formula IV-A:

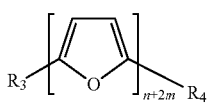

IV-A wherein [n+2m] are as described for formula IV and $R_3$ and $R_4$ are independently an alkyl chain between 2-18 carbons. In another embodiment, $R_3$ and $R_4$ are independently an alkyl chain between 2 to 12 carbons. In another embodiment, $R_3$ and $R_4$ are independently an alkyl chain between 2 to 10 carbons. In another embodiment, $R_3$ and $R_4$ are independently an alkyl chain between 2 to 8 carbons. In another embodiment, $R_3$ and $R_4$ are independently an alkyl chain between 3 to 8 carbons. In another embodiment, $R_3$ and $R_4$ are independently an alkyl chain having 6 carbons. In another embodiment, $R_3$ and $R_4$ are independently a substituted or unsubstituted phenyl ring. In another embodiment, $R_3$ and $R_4$ are independently a phenyl ring substituted by a halogen. In another embodiment, $R_3$ and $R_4$ are independently a phenyl ring substituted by between 1-5 fluorine (F) groups. In another embodiment, $R_3$ and $R_4$ are independently a phenyl ring substituted by penta-fluorine. In another embodiment, $R_3$ and $R_4$ are independently aryl, cycloalkyl and heteroaryl groups.

In one embodiment, this invention is directed to an oligofuran represented by the structure of formula DH-6F wherein the oligofuran possess dihexyl chains and sexifuran groups:

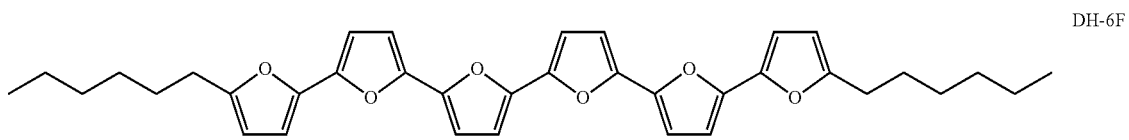 [SMILES: CCCCCCc1ccc(-c2ccc(-c3ccc(-c4ccc(-c5ccc(-c6ccc(CCCCCC)o6)o5)o4)o3)o2)o1]

DH-6F

In one embodiment, this invention is directed to an oligofuran represented by the structure of formula DPFB-6F:

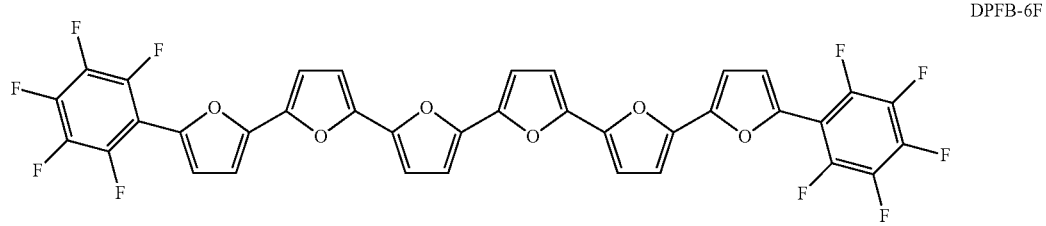 [SMILES: Fc1c(F)c(F)c(-c2ccc(-c3ccc(-c4ccc(-c5ccc(-c6ccc(-c7ccc(-c8c(F)c(F)c(F)c(F)c8F)o7)o6)o5)o4)o3)o2)c(F)c1F]

DPFB-6F

In one embodiment, this invention provides a process for the preparation oligofurans and polyfurans.

In one embodiment, this invention provides a process for the preparation of oligofuran of formula III(n+2m) comprising reacting a compound represented by the structure of formula I:

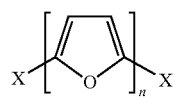
I(n)

with 2-(tributyltin)-oligofuran of formula II:

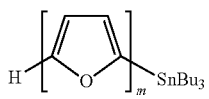
II(m)

to yield oligofuran of formula III (n+2m):

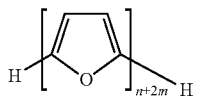
III(n + 2m)

wherein X is Br or I;
n is an integer between 1-20; and
m is an integer between 1-20.

In one embodiment, this invention provides a process for the preparation of oligofuran of formula IV(n+2m) comprising reacting a compound represented by the structure of formula V(n):

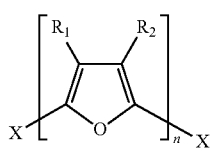
V(n)

with 2-(tributyltin)-oligofuran of formula VI(m):

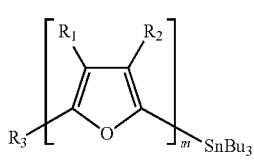
VI(m)

to yield oligofuran of formula IV(n+2m):

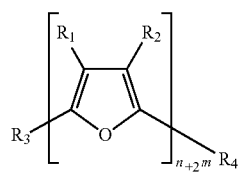
IV(n + 2m)

wherein
$R_1$, $R_2$, $R_3$ and $R_4$ are independently hydrogen, $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocycloalkyl, ($C_0$-$C_{18}$ alkyl)-aryl, ($C_0$-$C_{18}$ alkyl)-heteroaryl, CN, $CO_2H$, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)($C_1$-$C_{18}$ alkyl)], halo-($C_1$-$C_{18}$ alkyl), hydroxyl-($C_1$-$C_{18}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), NHC(O)($C_1$-$C_6$ alkyl) or N[($C_1$-$C_6$ alkyl)][C(O)($C_1$-$C_6$ alkyl)];
or
$R_1$ and $R_2$ combine to form a 4-8 membered ring comprising 0-3 double bonds and 0-3 heteroatoms selected from O, N, Se or S wherein said 4-8 membered ring is optionally substituted with 1-3 groups comprising $C_1$-$C_{18}$-alkyl, ($C_0$-$C_6$ alkyl)-cycloalkyl, ($C_0$-$C_6$ alkyl)-aryl, ($C_0$-$C_6$ alkyl)-heteroaryl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), dialkylamine, NHC(O)($C_1$-$C_6$ alkyl) or N[($C_1$-$C_6$ alkyl)][C(O)($C_1$-$C_6$ alkyl)]; wherein said aryl, cycloalkyl and heteroaryl groups of said ($C_0$-$C_6$ alkyl)-aryl, ($C_0$-$C_6$ alkyl)-cycloalkyl and ($C_0$-$C_6$ alkyl)-heteroaryl groups are optionally substituted with 1-3 groups comprising halide, $C_1$-$C_6$ alkyl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), N($R_4$)($R_5$), NHC(O)($C_1$-$C_6$ alkyl) or N[($C_1$-$C_6$ alkyl)][C(O)($C_1$-$C_6$ alkyl)]; and
X is Br or I.

In one embodiment, this invention provides a process for the preparation of oligofuran of formula III (m+2n) comprising reacting a compound represented by the structure of formula VII:

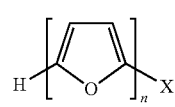
VII(n)

with 2,5-(tributyltin)-oligofuran of formula VIII:

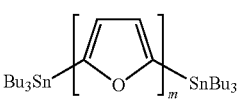
VIII(m)

to yield oligofuran of formula III:

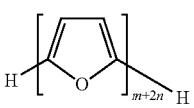
III(m + 2n)

wherein X is Br or I;
n is an integer between 1-20; and
m is an integer between 1-20, wherein m+2n is not 3 or 4.

In one embodiment, this invention provides a process for the preparation of oligofuran of formula IV(m+2n) comprising reacting a compound represented by the structure of formula IX:

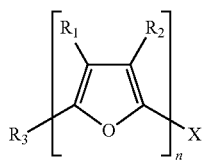

with 2,5-(tributyltin)-oligofuran of formula X:

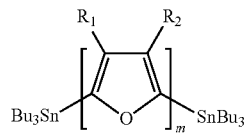

to yield oligofuran of formula IV(m+2n):

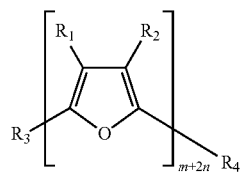

wherein
$R_1, R_2, R_3$ and $R_4$ are independently hydrogen, $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocycloalkyl, ($C_0$-$C_{18}$ alkyl)-aryl, ($C_0$-$C_{18}$ alkyl)-heteroaryl, CN, $CO_2H$, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)($C_1$-$C_{18}$ alkyl)], halo-($C_1$-$C_{18}$ alkyl), hydroxyl-($C_1$-$C_{18}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), NHC(O)($C_1$-$C_6$ alkyl) or N[($C_1$-$C_6$ alkyl)][C(O)($C_1$-$C_6$ alkyl)];
or
$R_1$ and $R_2$ combine to form a 4-8 membered ring comprising 0-3 double bonds and 0-3 heteroatoms selected from O, N, Se or S wherein said 4-8 membered ring is optionally substituted with 1-3 groups comprising $C_1$-$C_{18}$-alkyl, ($C_0$-$C_6$ alkyl)-cycloalkyl, ($C_0$-$C_6$ alkyl)-aryl, ($C_0$-$C_6$ alkyl)-heteroaryl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), dialkylamine, NHC(O)($C_1$-$C_6$ alkyl) or N[($C_1$-$C_6$ alkyl)][C(O)($C_1$-$C_6$ alkyl)]; wherein said aryl, cycloalkyl and heteroaryl groups of said ($C_0$-$C_6$ alkyl)-aryl, ($C_0$-$C_6$ alkyl)-cycloalkyl and ($C_0$-$C_6$ alkyl)-heteroaryl groups are optionally substituted with 1-3 groups comprising halide, $C_1$-$C_6$ alkyl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), $N(R_4)(R_5)$, NHC(O) ($C_1$-$C_6$ alkyl) or N[($C_1$-$C_6$ alkyl)][C(O)($C_1$-$C_6$ alkyl)];
X is Br or I;
m is an integer between 1-50; and
n is an integer between 1-50;

In one embodiment, this invention provides an oligofuran of formula III(m+2n) prepared by the process described herein above. In another embodiment, this invention provides an oligofuran of formula III(n+2m) prepared by the process described herein above.

In one embodiment, this invention provides an oligofuran of formula IV(m+2n) prepared by the process described herein above. In another embodiment, this invention provides an oligofuran of formula IV(n+2m) prepared by the process described herein above.

In another embodiment this invention provide an oligofuran represented by the structure of formula I:

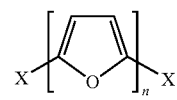

wherein X is Br or I; and
n is between 1-20.

In another embodiment this invention provide an oligofuran represented by the structure of formula II:

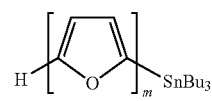

wherein m is between 1-20.

In another embodiment this invention provide an oligofuran represented by the structure of formula V:

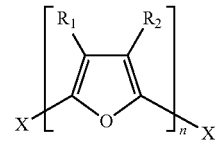

wherein X is Br or I;
n is between 1-50;
and $R_1$ and $R_2$ are as described for formula IV.

In another embodiment this invention provide an oligofuran represented by the structure of formula VI:

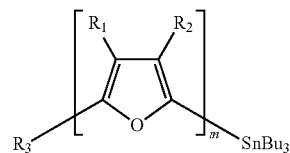

wherein m is between 1-50 and $R_1$, $R_2$ and $R_3$ are as described for formula IV.

In another embodiment this invention provide an oligfuran represented by the structure of formula VII:

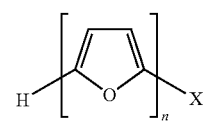

wherein X is Br or I; and
n is between 1-20.

In another embodiment this invention provide an oligfuran represented by the structure of formula VIII

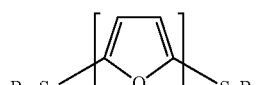

wherein m is between 1-20.

In another embodiment this invention provide an oligfuran represented by the structure of formula VIII:

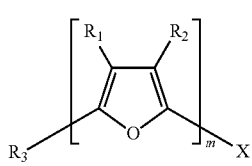

wherein X is Br or I;
m is between 1-50 and $R_1$, $R_2$ and $R_3$ are as described for formula IV.

In another embodiment this invention provide an oligofuran represented by the structure of formula X:

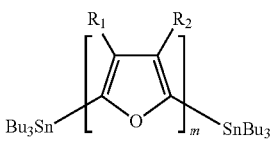

wherein m is between 1-50 and $R_1$ and $R_2$ are as described for formula IV.

In another embodiment this invention provide an oligofuran represented by the structure of formula XI:

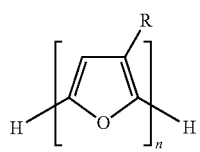

wherein n is between 4-50; and
R is linear or branched $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocloalkyl, ($C_0$-$C_{18}$ alkyl)-aryl, ($C_0$-$C_{18}$ alkyl)-heteroaryl, CN, $CO_2H$, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)($C_1$-$C_{18}$ alkyl)], halo-($C_1$-$C_{18}$ alkyl), hydroxyl-($C_1$-$C_{10}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2H$, OH, SH, $NH_2$, $CO_2$—($C_1$-$C_6$ alkyl), O—($C_1$-$C_6$alkyl), S—($C_1$-$C_6$ alkyl), NH($C_1$-$C_6$ alkyl), NHC(O)($C_1$-$C_6$alkyl) or N[($C_1$-$C_6$ alkyl)][C(O)($C_1$-$C_6$ alkyl)].

In another embodiment this invention provide an oligfuran represented by the structure of formula XII:

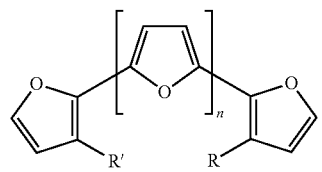

wherein n is between 4-50; and R and R' are independently hydrogen, linear or branched $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocycloalkyl, ($C_0$-$C_{18}$ alkyl)-aryl, ($C_0$-$C_{18}$ alkyl)-heteroaryl, CN, $CO_2H$, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)($C_1$-$C_{18}$ alkyl)], halo-($C_1$-$C_{18}$ alkyl), hydroxyl-($C_1$-$C_{18}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2H$, OH, SH, $NH_2$, $CO_2$—($C_1$-$C_6$ alkyl), O—($C_1$-$C_6$alkyl), S—($C_1$-$C_6$ alkyl), NH($C_1$-$C_6$ alkyl), NHC(O)($C_1$-$C_6$alkyl) or N[($C_1$-$C_6$ alkyl)][C(O)($C_1$-$C_6$ alkyl)].

Figure 20:
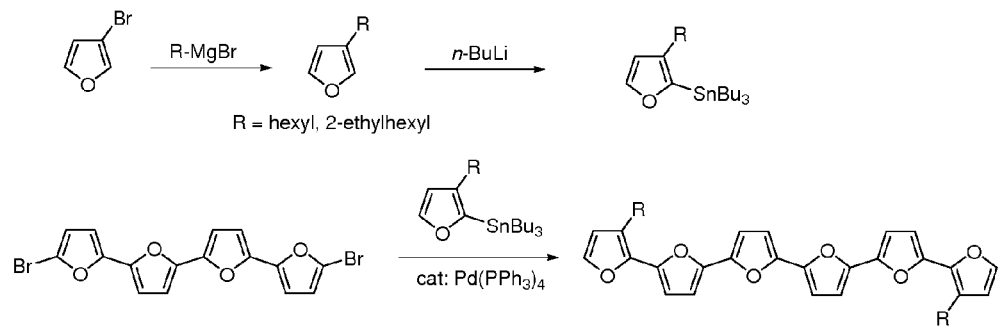
FIG. 20 depicts a synthetic route to long β-alkyl-oligofurans.
Figure 21:
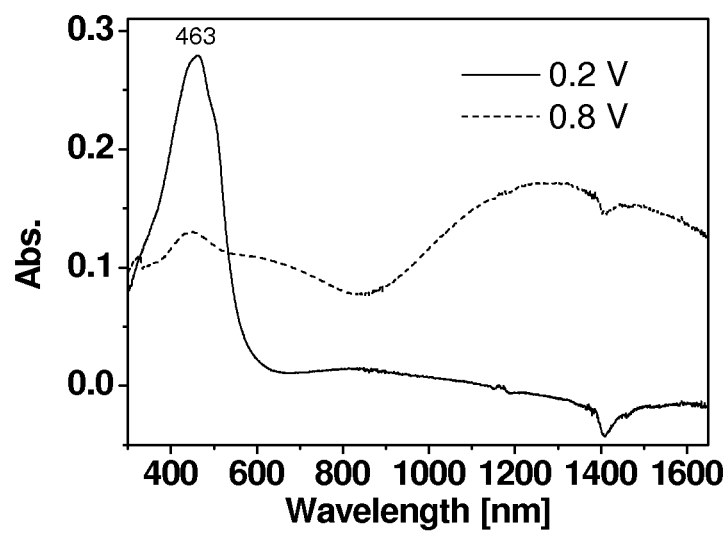
FIG. 21 depicts spectroelectrochemistry of 3"-octyl-5F as a function of applied potential in acetonitrile (electrolyte: TBA-$CF_3SO_3$ 0.1 M, working electrode: ITO on glass, counter electrode: Pt disk, reference electrode Ag/AgCl).

In one embodiment R and/or R' of formula XI and XII is a linear or branched alkyl. In another embodiment R and/or R' of formula XI and XII is a haloakyl. In another embodiment R and/or R' of formula XI and XII is ethyl hexyl. In another embodiment R and/or R' of formula XI and XII is hexyl. In another embodiment R and/or R' of formula XI and XII is methyl. In another embodiment R and/or R' of formula XI and XII is an aryl. In another embodiment R and/or R' of formula XI and XII is a phenyl. In another embodiment R and/or R' of formula XI and XII is an halo-aryl. In another embodiment R and/or R' of formula XI and XII is an alkyl-phenyl. In another embodiment R and/or R' of formula XI and XII is an alkyl-halophenyl. In another embodiment R and/or R' of formula XI and XII is pentaflurobenzene. In another embodiment R and/or R' of formula XI and XII is aklkyl-pentaflurobenzene. In another embodiment R and/or R' of formula XI and XII is an alkyl-phenyl wherein the phenyl is substituted with between 1-5 fluoro groups. In another embodiment R and/or R' of formula XI and XII is an aryl wherein the aryl is substituted with between 1-5 fluoro groups. In another embodiment, the synthesis of exemplified oligofuran of formula XII is depicted in FIG. 20.

In another embodiment this invention provide an oligfuran represented by the structure of formula XIII:

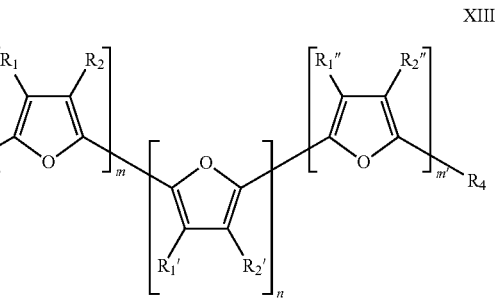

wherein $R_1$, $R_1'$, $R_1''$, $R_2$, $R_2'$, $R_2''$, $R_3$ and $R_4$ are independently hydrogen, $C_1$-$C_{18}$ alkyl, $C_1$-$C_{18}$ alkenyl, $C_1$-$C_{18}$ alkynyl, ($C_0$-$C_6$ alkyl)-cycloalkyl, ($C_0$-$C_6$ alkyl)-heterocycloalkyl, ($C_0$-$C_{18}$ alkyl)-aryl, ($C_0$-$C_{18}$ alkyl)-heteroaryl, CN, $CO_2H$, OH, SH, $NH_2$, $NO_2$, halogen, $CO_2$—($C_1$-$C_{18}$ alkyl), O—($C_1$-$C_{18}$ alkyl), S—($C_1$-$C_{18}$ alkyl), NH($C_1$-$C_{18}$ alkyl), NHC(O)($C_1$-$C_{18}$ alkyl) or N[($C_1$-$C_{18}$ alkyl)][C(O)

($C_1$-$C_{18}$ alkyl)], halo-($C_1$-$C_{18}$ alkyl), hydroxyl-($C_1$-$C_{18}$ alkyl), amino-($C_1$-$C_{18}$ alkyl), phenyl, aryl, cycloalkyl or heteroaryl; wherein said alkyl, aryl, cycloalkyl and heteroaryl groups are optionally substituted with 1-3 groups comprising halide, [$C_1$-$C_6$ alkyl], CN, $CO_2H$, OH, SH, $NH_2$, $CO_2$—($C_1$-$C_6$ alkyl), O—($C_1$-$C_6$alkyl), S—($C_1$-$C_6$ alkyl), NH($C_1$-$C_6$ alkyl), NHC(O)($C_1$-$C_6$alkyl) or N[($C_1$-$C_6$ alkyl)][C(O)($C_1$-$C_6$ alkyl)];

or $R_1$ and $R_2$; $R_1'$ and $R_2'$; $R_1''$ and $R_2''$ combine to form a 4-8 membered ring comprising 0-3 double bonds and 0-3 heteroatoms selected from O, N, Se or S wherein said 4-8 membered ring is optionally substituted with 1-3 groups comprising $C_1$-$C_{18}$-alkyl, ($C_0$-$C_6$ alkyl)-cycloalkyl, ($C_0$-$C_6$ alkyl)-aryl, ($C_0$-$C_6$ alkyl)-heteroaryl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), dialkylamine, NHC(O)($C_1$-$C_6$ alkyl) or N[($C_1$-$C_6$ alkyl)][C(O)($C_1$-$C_6$ alkyl)]; wherein said aryl, cycloalkyl and heteroaryl groups of said ($C_0$-$C_6$ alkyl)-aryl, ($C_0$-$C_6$ alkyl)-cycloalkyl and ($C_0$-$C_6$ alkyl)-heteroaryl groups are optionally substituted with 1-3 groups comprising halide, $C_1$-$C_6$ alkyl, CN, $CO_2H$, OH, SH, $NH_2$, $CO_2$—($C_1$-$C_6$ alkyl), O—($C_1$-$C_6$ alkyl), S—($C_1$-$C_6$ alkyl), NH($C_1$-$C_6$ alkyl), N($R_4$)($R_5$), NHC(O)($C_1$-$C_6$ alkyl) or N[($C_1$-$C_6$ alkyl)][C(O)($C_1$-$C_6$ alkyl)];

m is an integer between 1-50;
m' is an integer between 0-50 and
n is an integer between 1-50;
wherein if $R_1$, $R_1'$, $R_1''$ and $R_2$, $R_2'$, $R_2''$ are hydrogens then [n+m+m'] is not 3 or 4.

Figure 19:
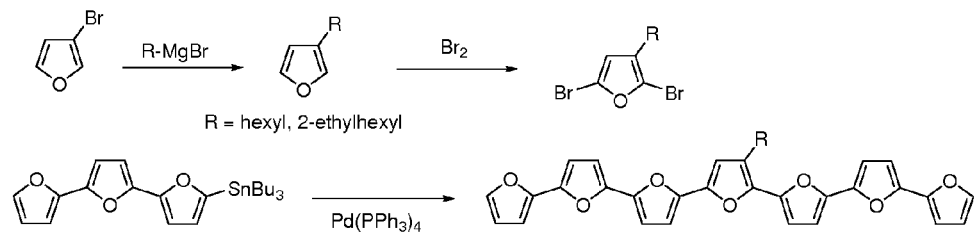
FIG. 19 depicts a synthetic route to long β-alkyl-oligofurans.
Figure 19:
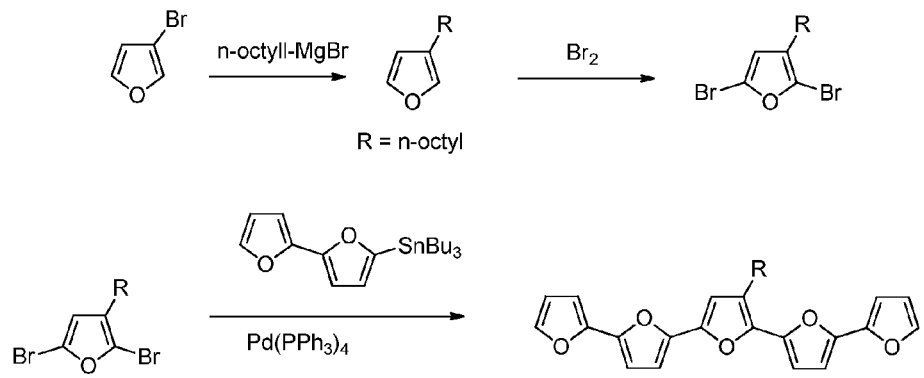

In one embodiment, $R_1$, $R_1'$, $R_1''$ and $R_2$, $R_2'$, $R_2''$ of the oligomer of formula XIII are the same. In another embodiment $R_1$, $R_1'$, $R_1''$ and $R_2$, $R_2'$, $R_2''$ of the oligomer of formula XIII are different. In another embodiment $R_1$, $R_1'$, $R_1''$ of formula XIII is hydrogen. In another embodiment $R_2$, $R_2'$, $R_2''$ of formula XIII is hydrogen. In another embodiment $R_1$, $R_1'$, $R_1''$, $R_2$, $R_2'$ and $R_2''$ of formula XIII are independently an alkyl. In another embodiment $R_1$, $R_1'$, $R_1''$, $R_2$, $R_2'$ and $R_2''$ of formula XIII are independently hydroxyalkyl. In another embodiment $R_1$, $R_1'$, $R_1''$, $R_2$, $R_2'$ and $R_2''$ of formula XIII are independently halo-alkyl. In another embodiment $R_1$, $R_1'$, $R_1''$, $R_2$, $R_2'$ and $R_2''$ of formula XIII are independently alkyl-aryl. In another embodiment $R_1$, $R_1'$, $R_1''$, $R_2$, $R_2'$ and $R_2''$ of formula XIII are independently cycloalkyl, hetrocycloalkyl, aryl, or heteroaryl. In one embodiment $R_1$, $R_1'$, $R_1''$, $R_2$, $R_2'$ and $R_2''$ of formula XIII are independently a linear or branched alkyl. In another embodiment $R_1$, $R_1'$, $R_1''$, $R_2$, $R_2'$ and $R_2''$ of formula XIII are independently a haloakyl. In another embodiment $R_1$, $R_1'$, $R_1''$, $R_2$, $R_2'$ and $R_2''$ of formula XIII are independently ethyl hexyl. In another embodiment $R_1$, $R_1'$, $R_1''$, $R_2$, $R_2'$ and $R_2''$ of formula XIII are independently hexyl. In another embodiment $R_1$, $R_1'$, $R_1''$, $R_2$, $R_2'$ and $R_2''$ of formula XIII are independently methyl. In another embodiment $R_1$, $R_1'$, $R_1''$, $R_2$, $R_2'$ and $R_2''$ of formula XIII are independently an aryl. In another embodiment In another embodiment $R_1$, $R_1'$, $R_1''$, $R_2$, $R_2'$ and $R_2''$ of formula XIII are independently phenyl. In another embodiment In another embodiment $R_1$, $R_1'$, $R_1''$, $R_2$, $R_2'$ and $R_2''$ of formula XIII are independently halo-aryl. In another embodiment In another embodiment $R_1$, $R_1'$, $R_1''$, $R_2$, $R_2'$ and $R_2''$ of formula XIII are independently alkyl-phenyl. In another embodiment In another embodiment $R_1$, $R_1'$, $R_1''$, $R_2$, $R_2'$ and $R_2''$ of formula XIII are independently alkyl-halophenyl. In another embodiment In another embodiment $R_1$, $R_1'$, $R_1''$, $R_2$, $R_2'$ and $R_2''$ of formula XIII are independently pentaflurobenzene. In another embodiment In another embodiment $R_1$, $R_1'$, $R_1''$, $R_2$, $R_2'$ and $R_2''$ of formula XIII are independently aklkyl-pentaflurobenzene. In another embodiment In another embodiment $R_1$, $R_1'$, $R_1''$, $R_2$, $R_2'$ and $R_2''$ of formula XIII are independently an alkyl-phenyl wherein the phenyl is substituted with between 1-5 fluoro groups. In another embodiment In another embodiment $R_1$, $R_1'$, $R_1''$, $R_2$, $R_2'$ and $R_2''$ of formula XIII are independently aryl wherein the aryl is substituted with between 1-5 fluoro groups. In another embodiment, the synthesis of exemplified oligofuran of formula XII is depicted in FIG. 19.

In one embodiment, the oligofuran of formula XIII comprises a furan repeating units, wherein only between 10-50% of the repeating units are substituted. In another embodiment between 10-50% of the repeating units are mono-substituted. In another embodiment between 10-50% of the repeating units are di-substituted. In another embodiment at least one of the repeating units is mono or di-substituted.

In one embodiment, $R_3$ and $R_4$ of the oligomer of formula XIII are the same. In another embodiment $R_3$ and $R_4$ of the oligomer of formula XIII are different. In another embodiment $R_3$ of formula IV is hydrogen. In another embodiment $R_4$ of formula XIII is hydrogen. In another embodiment $R_3$ and $R_4$ of formula XIII are hydrogens. In another embodiment $R_3$ and $R_4$ are not hydrogens. In another embodiment $R_3$ of formula XIII is an alkyl. In another embodiment $R_4$ of formula XIII is an alkyl. In another embodiment $R_3$ and $R_4$ are an alkyl. In another embodiment $R_3$ and $R_3$ are O-alkyl. In another embodiment $R_3$ and $R_4$ are methoxy group. In another embodiment $R_3$ and $R_4$ are hexyl. In another embodiment $R_3$ and $R_4$ are methoxy group. In another embodiment $R_3$ and $R_4$ are methyl. In another embodiment $R_3$ and $R_4$ are methoxy group. In another embodiment $R_3$ and $R_4$ are ethyl-hexyl. In another embodiment $R_3$ and $R_4$ are alkyl-phenyl; In another embodiment $R_3$ and $R_4$ are alkyl-pentafluorophenyl. In another embodiment $R_3$ and $R_4$ are alkyl-fluorophenyl; In another embodiment $R_3$ and $R_4$ of formula XIII are independently hydroxyalkyl; In another embodiment $R_3$ and $R_4$ of formula XIII are independently halo-alkyl. In another embodiment $R_3$ and $R_4$ of formula XIII are independently alkyl-aryl; In another embodiment $R_3$ and $R_4$ of formula XIII are independently cycloalkyl, hetrocycloalkyl, aryl, or heteroaryl.

In one embodiment, an oligomer of formula XIII is represented by the following structure:

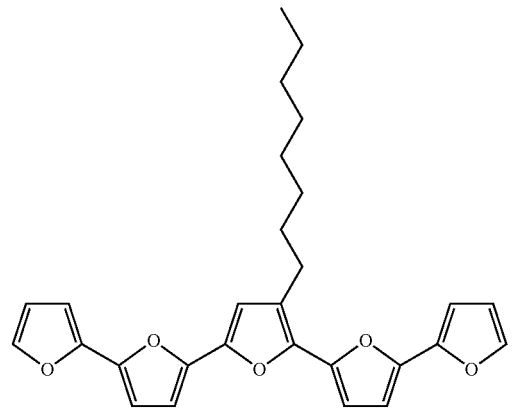

3"-octyl-5F

In one embodiment, an oligomer of formula XIII is represented by the following structure:

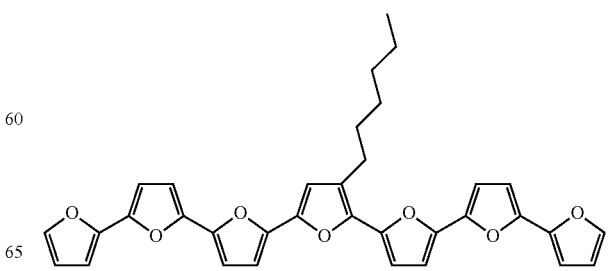

4"-hexyl-7F

In another embodiment, the synthesis of the above structures (3"-octyl-5F and 4"-hexyl-7F) is depicted in FIG. 19.

In one embodiment [n] of the oligomers of this invention is an integer between 1-20. In another embodiment, [n] of the oligomers of this invention is an integer between 1-50. In another embodiment, [n] of the oligomers of this invention is an integer between 1-10. In another embodiment, [n] of the oligomers of this invention is an integer between 1-5. In another embodiment, [n] of the oligomers of this invention is an integer between 5-10. In another embodiment, [n] of the oligomers of this invention is an integer between 20-30. In another embodiment, [n] of the oligomers of this invention is an integer between 25-50.

In one embodiment [m] of the oligomers of this invention is an integer between 1-20. In another embodiment, [m] of the oligomers of this invention is an integer between 1-50. In another embodiment, [m] of the oligomers of this invention is an integer between 1-10. In another embodiment, [m] of the oligomers of this invention is an integer between 1-5. In another embodiment, [m] of the oligomers of this invention is an integer between 5-10. In another embodiment, [n] of the oligomers of this invention is an integer between 20-30. In another embodiment, [n] of the oligomers of this invention is an integer between 25-50.

In another embodiment, the oligofurans of this invention comprise 5 repeating units. In one embodiment, the oligofurans of this invention comprise 6 repeating units. In one embodiment, the oligofurans of this invention comprise 7 repeating units. In one embodiment, the oligofurans of this invention comprise 8 repeating units. In one embodiment, the oligofurans of this invention comprise 9 repeating units. In one embodiment, the oligofurans of this invention comprise 10 repeating units. In one embodiment, the oligofurans of this invention comprise between 5-10 repeating units. In one embodiment, the oligofurans of this invention comprise between 5-15 repeating units. In one embodiment, the oligofurans of this invention comprise between 5-20 repeating units. In one embodiment, the oligofurans of this invention comprise between 5-30 repeating units. In one embodiment, the oligofurans of this invention comprise between 4-50 repeating units. In one embodiment, the oligofurans of this invention comprise between 10-15 repeating units. In one embodiment, the oligofurans of this invention comprise between 15-20 repeating units. In one embodiment, the oligofurans of this invention comprise between 20-25 repeating units. In one embodiment, the oligofurans of this invention comprise between 25-30 repeating units. In one embodiment, the oligofurans of this invention comprise between 30-40 repeating units. In one embodiment, the oligofurans of this invention comprise between 40-50 repeating units. In one embodiment, the oligofurans of this invention comprise between 50-60 repeating units. In one embodiment, the oligofurans of this invention comprise between 50-80 repeating units. In one embodiment, the oligofurans of this invention comprise between 80-100 repeating units. In one embodiment, the oligofurans of this invention comprise between 100-150 repeating units.

In one embodiment, the oligofurans of this invention comprise mono-substituted or bis-substituted repeating units of furan. In another embodiment, only between 10-50% of the furan repeating units are mono-substituted or bis-substituted. In another embodiment, 100% of the furan repeating units are mono-substituted or bis-substituted. In another embodiment, at least one of the furan repeating units is mono-substituted or bis-substituted.

An "alkyl" group refers, in one embodiment, to a saturated aliphatic hydrocarbon, including straight-chain, branched-chain and cyclic alkyl groups. In one embodiment, the alkyl group has 1-25 carbons. In one embodiment, the alkyl group has 1-18 carbons. In one embodiment, the alkyl group has 1-12 carbons. In one embodiment, the alkyl group has 1-15 carbons. In another embodiment, the alkyl group has 1-7 carbons. In one embodiment the alkyl in n-hexyl. In one embodiment the alkyl is methyl. In one embodiment the alkyl in n-octyl. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, in one embodiment by F, in another embodiment by Cl, in another embodiment by Br, in another embodiment by I.

A "hydroxyalkyl" group refers to an alkyl group as defined above, which is substituted by one or hydroxyl groups.

A "cycloalkyl" group refers to a cyclic group having at least one saturated carbocyclic group which may be unsubstituted or substituted by one or more groups selected from halogen, haloalkyl, hydroxy, alkoxy, carbonyl, amido, alkylamido, dialkylamido, nitro, amino, alkylamino, dialkylamino, carboxy or thio or thioalkyl. Nonlimiting examples of cycloalkyl rings are cyclopropane, cyclobutane, cyclopentane, cyclohexane, cycloheptane, cyclooctane, and the like. In one embodiment, the cycloalkyl group is a 3-12 membered ring. In another embodiment, the cycloalkyl group is a 3-8 membered ring. In another embodiment, the cycloalkyl group comprises of 1-4 fused rings.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy, carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, quinolyl, isoquinolyl, and the like. In one embodiment, the aryl group is a 3-12 membered ring. In another embodiment, the aryl group is a 3-8 membered ring. In another embodiment, the aryl group comprises 3-4 fused rings A "hydroxyl" group refers to an OH group.

The term "halogen" refers to in one embodiment to F, in another embodiment to Cl, in another embodiment to Br, in another embodiment to I.

The term "ring" refers to a monocyclic or bicyclic aromatic or aliphatic ring system comprising 3-10 atoms. In one embodiment, said ring contains 0-4 heteroatoms selected from 0, N and S. In another embodiment, said ring is optionally substituted with 0-3 groups. In another embodiment, said ring is cyclohexane. In another embodiment, said ring is cyclopentane. In another embodiment, said ring is benzene. In another embodiment, said ring is naphthalene. In another embodiment, said ring is piperazine. In another embodiment, said ring is quinoline.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

The term "substituted" refers to substitution of one or more hydrogens with non-hydrogen groups. Non-limiting examples of non-hydrogen groups includes alkyl, alkenyl, alkynyl, haloalkyl, aryl, hydroxyl, alkoxyl, cyano, amido, carboxyl, amino, halogen, etc.

An "alkenyl" group refers, in another embodiment, to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkynyl" group refers, in another embodiment, to an unsaturated hydrocarbon, including straight chain, branched chain and cyclic groups having one or more triple bond. The alkynyl group may have one triple bond, two triple bonds, three triple bonds etc. Examples of alkynyl groups are ethynyl, propynyl, butynyl, etc. The alkynyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

In one embodiment, this invention provides a process for the preparation of polyfuran of formula III comprising:
(a) brominating oligofuran of formula III(m+2n) or oligofuran of formula III(n+2m) to yield the corresponding 2,5-dibromo-oligofuran or 2-bromo-oligofuran;
(b) reacting oligofuran of formula III(m+2n) or oligofuran of formula III(n+2m) with tributyltin chloride to yield the corresponding 2-tributyltin-oligofuran or 2,5-bis(tributyl)tin-oligofuran;
(c) reacting 2,5-dibromo-oligofuran or 2-bromo-oligofuran of step (a) with 2-tributyltin-oligofuran or 2,5-bis(tributyl)tin-oligofuran of step (b) in the presence of tetrakis(triphenylphosphine)palladium $Pd(PPh_3)_4$ to yield a polyfuran chain of formula III.

In another embodiment, steps (a-c) are repeated to obtain a longer chain of polyfuran of formula III.

In one embodiment, this invention provides a process for the preparation of polyfuran of formula IV comprising:
(a) brominating oligofuran of formula IV(m+2n) or oligofuran of formula IV(n+2m) to yield the corresponding 2,5-dibromo-oligofuran or 2-bromo-oligofuran;
(b) reacting oligofuran of formula IV(m+2n) or oligofuran of formula IV(n+2m) with tributyltin chloride to yield the corresponding 2-tributyltin-oligofuran or 2,5-bis(tributyl)tin -oligofuran;
(c) reacting 2,5-dibromo-oligofuran or 2-bromo-oligofuran of step (a) with 2-tributyltin-oligofuran or 2,5-bis(tributyl)tin-oligofuran of step (b) in the presence of tetrakis(triphenylphosphine)palladium $Pd(PPh_3)_4$ to yield a polyfuran chain of formula IV.

In another embodiment, steps (a-c) are repeated to obtain a longer chain of polyfuran of formula IV.

In another embodiment 2,5-dibromo-oligofuran reacts with 2-tributyltin-oligofuran. In another embodiment, 2-bromo-oligofuran reacts with 2,5-bis(tributyl)tin-oligofuran. In another embodiment, 2,5-bis(tributyl)tin-oligofuran reacts with 2,5-dibromo-oligofuran.

In one embodiment, this invention provides a polyfuran or oligofuran of formula III or IV prepared according to the process described in this invention. In one embodiment, this invention provides a polyfuran or oligofuran of formula III or IV prepared according to the process described in this invention.

In one embodiment, the process of this invention for the preparation of oligofuran or polyfuran of formula III or IV comprising reacting a 2,5 dibromo-oligofuran or 2-bromo-oligofuran with 2-tributyltin oligofuran or 2,5-bis(tributyl)tin-oligofuran. In another embodiment, the reaction is in the presence of tetrakis(triphenylphosphine)palladium [$Pd(PPh_3)_4$].

In one embodiment, this invention provides a process for the preparation of oligofuran or polyfuran, wherein 2,5-dibromo-oligofuran or 2-bromo-oligofuran is one of the reactants. In another embodiment, the 2,5-dibromo-oligofuran or 2-bromo-oligofuran is prepared by bromination of the corresponding oligofuran.

In another embodiment, the bromination is in the presence of N-bromosuccinimide (NBS). In another embodiment, the bromination is according to Fumio et al., *Bull. Chem. Soc. Jpn.* 63, 2828 (1990), which is incorporated herein by reference.

In one embodiment, this invention provides a process for the preparation of polyfuran of formula III comprising:
(a) iodination of oligofuran of formula III(m+2n) or oligofuran of formula III(n+2m) to yield the corresponding 2,5-diiodo-oligofuran or 2-iodo-oligofuran;
(b) reaction of oligofuran of formula III(m+2n) or oligofuran of formula III(n+2m) with tributyltin chloride to yield the corresponding 2-tributyltin-oligofuran or 2,5-bis(tributyl)tin-oligofuran;
(c) reacting 2,5-diiodo-oligofuran or 2-iodo-oligofuran of step (a) with 2-tributyltin-oligofuran or 2,5-bis(tributyl)tin-oligofuran of step (b) in the presence of tetrakis(triphenylphosphine)palladium $Pd(PPh_3)_4$ to yield a polyfuran chain of formula III.

In another embodiment, steps (a-c) are repeated to obtain a longer chain of polyfuran of formula III.

In one embodiment, this invention provides a process for the preparation of polyfuran of formula IV comprising:
(a) iodination of oligofuran of formula IV(m+2n) or oligofuran of formula IV(n+2m) to yield the corresponding 2,5-diiodo-oligofuran or 2-iodo-oligofuran;
(b) reacting oligofuran of formula IV(m+2n) or oligofuran of formula IV(n+2m) with tributyltin chloride to yield the corresponding 2-tributyltin-oligofuran or 2,5-bis(tributyl)tin -oligofuran;
(c) reacting 2,5-diiodo-oligofuran or 2-iodo-oligofuran of step (a) with 2-tributyltin-oligofuran or 2,5-bis(tributyl)tin-oligofuran of step (b) in the presence of tetrakis(triphenylphosphine)palladium $Pd(PPh_3)_4$ to yield a polyfuran chain of formula IV.

In another embodiment, steps (a-c) are repeated to obtain a longer chain of polyfuran of formula IV.

In another embodiment 2,5-diiodo-oligofuran reacts with 2-tributyltin-oligofuran. In another embodiment, 2-iodo-oligofuran reacts with 2,5-bis(tributyl)tin-oligofuran. In another embodiment, 2,5-bis(tributyl)tin-oligofuran reacts with 2,5-diiodo-oligofuran.

In one embodiment, this invention provides a polyfuran or oligofuran of formula III or IV prepared according to the process described in this invention. In one embodiment, this invention provides a polyfuran or oligofuran of formula III or IV prepared according to the process described in this invention.

In one embodiment, the process of this invention for the preparation of oligofuran or polyfuran of formula III or IV comprising reacting a 2,5 diiodo-oligofuran or 2-iodo -oligofuran with 2-tributyltin oligofuran or 2,5-bis(tributyl)tin-oligofuran. In another embodiment, the reaction is in the presence of tetrakis(triphenylphosphine)palladium [Pd(PPh$_3$)$_4$].

In one embodiment, this invention provides a process for the preparation of oligofuran or polyfuran, wherein 2,5-diiodo-oligofuran or 2-iodo-oligofuran is one of the reactants. In another embodiment, the 2,5-diiodo-oligofuran or 2-iodo-oligofuran is prepared by bromination of the corresponding oligofuran.

In one embodiment, this invention provides a process for the preparation of oligofuran or polyfuran, wherein 2-tributyltin-oligofuran or 2,5-bis(tributyl)tin -oligofuran is one of the reactants. In another embodiment, 2-tributyltin-oligofuran or 2,5-bis(tributyl)tin-oligofuran is prepared by derivatizing the corresponding oligofuran with butyllithium followed by tributylthin-chloride. In another embodiment, Stille coupling between tin-oligofurans and bromo-oligofurans or iodo-oligofuran is followed by reduced vacuum sublimation of the filtrate to yield oligofuran.

In one embodiment, furans can be obtained from renewable resources. In another embodiment, the oligofurans of this invention are biodegradable. In another embodiment, this invention is directed to biodegradable oligofuran based on renewable resources.

In one embodiment, furan can be prepared from renewable sources of mono, oligo and polysaccharides such as cellulose polymer, glucose, fructose, corn cobs, oat, rice hulls, sugarcane, cotton seeds, olive husks and stones. The reaction sequence leading to furan first goes through acid-catalyzed hydrolysis of the polymeric pentoses or hexoses to the corresponding monosaccharide, followed by acid-catalyzed dehydration, and finally cyclization to give furan which can be used for polymer syntheses. In another embodiment, lignocellulosic biomass is a renewable resource for fuels and chemicals (such as furan) by using N,N dimethylacetamide (DMA) and lithium chloride (LiCl) through catalysis by Bronsted acids. (e.g. H$_2$SO$_4$) as described in Joseph B. Binder and Ronald T Raines, *JACS,* 2009, 131, 1979-1985, which is incorporated herein by reference.

In one embodiment, the oligofuran of this invention is biodegradable. In another embodiment, the oligofuran of this invention degrade enzymatically using lipase including non limiting examples as *Porcine pancreas, Rhizopus Delmar* or *Pseudomonas* sp. In another embodiment, the oligofuran of this invention is biodegradable by soil burial. In another embodiment, a bacteria and/or a fungi are mainly responsible for the degradation by soil burial.

Enzymatic degradability is evaluated by the measurement of total organic carbon content (TOC) of aqueous solutions containing water-soluble degradation products.

Conjugated compounds, inherently possess low solubility. For many industrial applications processability from solution and therefore solubility is an essential requirement if an economically viable process is to be obtained. Therefore in one embodiment, the process of this invention provides oligofurans, with higher solubility compared for example to corresponding oligothiophenes that improves the ease of processability, and enables drop casting/spin casting techniques to be used (the solubility of 6F is 0.7 mg/mL compared to only <0.05 mg/mL for 6T-oligothiophene possessing 6 units) In another embodiment the substituted oligofurans of this invention (Oligofuran IV, IV-A, DH-6F, V, VI, IX, X, XI, XII and XIII) are more soluble than the unsubstituted oligomers of this invention. In another embodiment, R$_1$ and R$_2$ of oligofurans IV, V, VI, IX and X increase the solubility of the oligofurans of this invention. In another embodiment R, R', R$_1$, R$_1$', R$_1$", R$_2$, R$_2$', R$_2$" of oligofurans IV, IV-A, V, VI, IX, X, XI, XII and XIII improve the electronic properties of the oligofuran. In another embodiment R, R', R$_1$, R$_1$', R$_1$", R$_2$, R$_2$', R$_2$" of oligofurans W, IV-A, V, VI, IX, X, XI, XII and XIII improve the stability properties of the oligofuran.

In another embodiment, the oligofurans, polyfurans and copolymers prepared according to the process of this invention provide higher fluorescence and better packing (i.e shorter interplane distances) than the corresponding oligothiophenes.

In one embodiment, the oligofuran and polyfuran of this invention provide an efficient charge transport material (e.g., for OFETs) and as a luminescent material for organic light emission devices (OLEDs and OLETs). These advantages, as compared mainly to oligothiophenes (OTs), include: (i) higher fluorescence quantum yield (up to 75%), (ii) high rigidity and high planarity; (iii) high rigidity and high planarity, (iv) high charge mobility (v) better solubility compared to the corresponding oligothiophenes (Table 1) and (vi) Furan-containing polymers are biodegradable In one embodiment, the oligofuran and polyfuran of this invention provide higher fluorescence quantum yield than the corresponding oligothiophenes. Short OFs show a high fluorescent quantum yield in the deep blue spectral region that is very challenging for efficient electroluminescent devices.

Figure 7:
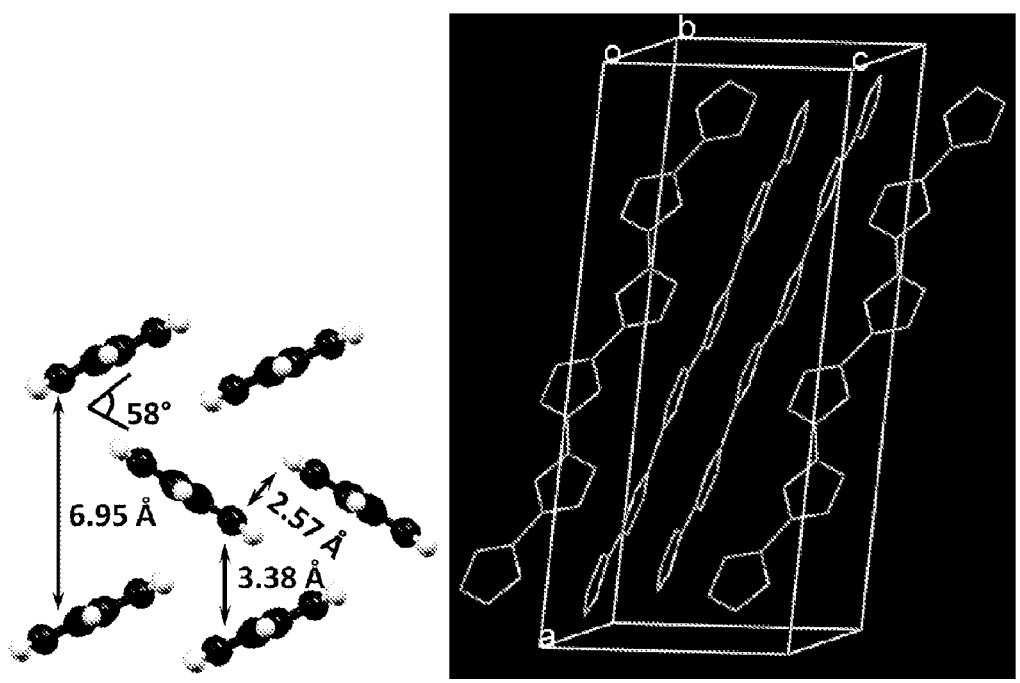
FIG. 7 Crystal packing of α-sexifuran (6F)
Figure 16:
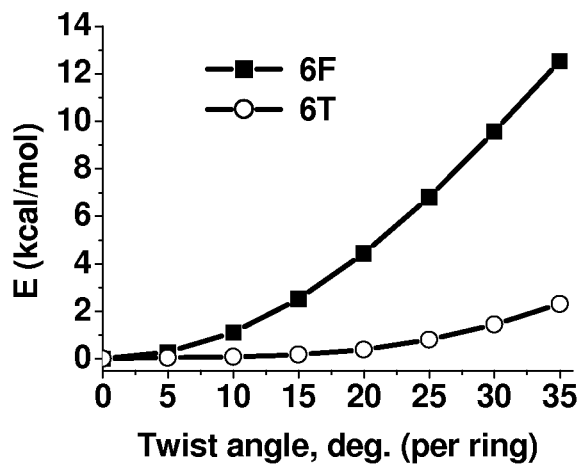
FIG. 16 depicts calculated (B3LYP/6-31G(d)) relative energy vs. twist angle required for spiral twisting of 6F and 6T.

In one embodiment, the oligofuran and polyfuran of this invention provide high rigidity and high planarity than the corresponding oligothiophenes. Oligofurans are significantly more rigid than oligothiophenes (FIG. 16). The high rigidity of OFs is seen in their significantly lower Stokes shift (around 0.25 eV for 3F-9F, and around 0.40 eV for 3T-6T, Table 1). Second, the optical absorption spectra of OFs in solution show a vibrational structure that is typically absent in OTs. The energy required to twist 6F is significantly greater than for 6T. Moreover, the high planarity is expected to facilitate dense solid-state packing that should result in good overlapping of molecular m-orbitals and hence enhanced charge transport properties. In one embodiment, the oligofuran of this invention maintain planarity better than oligothiophenes. In another embodiment, the X-ray structure of 6F i.e possessing 6 repeat units of furan) shows the oligomers to be completely planar, with herringbone packing, as for α-sexithiophene (6T), as presented in FIG. 7. The intermolecular distances are shorter compared to 6T. The distance between planes is 2.57 Å in 6F, which is significantly shorter than in 6T (2.89 Å), providing possible better charge mobility. Also the molecular density (obtained by dividing the number of molecules per unit cell volume) is 17% higher in 6F (oligofuran possessing six furan units) than in 6T (oligothiophene possessing six thiophene groups). In another embodiment, unlike thiophene analogues, 3F and 4F packing is not a herringbone.

In one embodiment, the oligofuran and polyfuran of this invention provide High charge mobility than the corresponding oligothiophenes. As OFs are more electron-rich and planar than OTs, one can expect OFs to have the potential to be good charge transport materials. Achievement of significant field effect mobility in oligofurans paves the way for their application in different devices based on nano-materials, such as OFETs, OLETs, and sensors. Therefore, oligofuran-based nanomaterials may be very promising, for example, for hole conduction.

In one embodiment, the oligofuran and polyfuran of this invention provide better solubility than the corresponding oligothiophenes. Solubility is among the key technological demands placed on materials for high-scale organic electronic nanotechnologies. Furans are more than an order of magnitude more soluble in common organic solvents than thiophenes, which allows unsubstituted furans to be processed from solution (e.g., by spin/drop/dip coating techniques). In addition, longer furans can be synthesized. This allows a greater variety of oligomers, with different emission wavelengths (from 350 nm for 3F up to 473 nm for 9F), allowing fine tuning of the solution emission spectra from the blue to green regions. In one embodiment, the solubility of the oligofuran of this invention is greater than the corresponding oligothiophenes. In another embodiment, oligofuran 6F (i.e possessing 6 repeat units of furan) in chloroform is over 10 times more soluble than the corresponding 6T (i.e possessing 6 repeat units of thiophene): 0.7 mg/mL compared to <0.05 mg/mL for 6T.

In one embodiment, the oligofuran and polyfuran of this invention are biodegradable, in contrast to their thiophene analogs and furans can be obtained from renewable resources, unlike other organic electronic materials.

Figure 3:
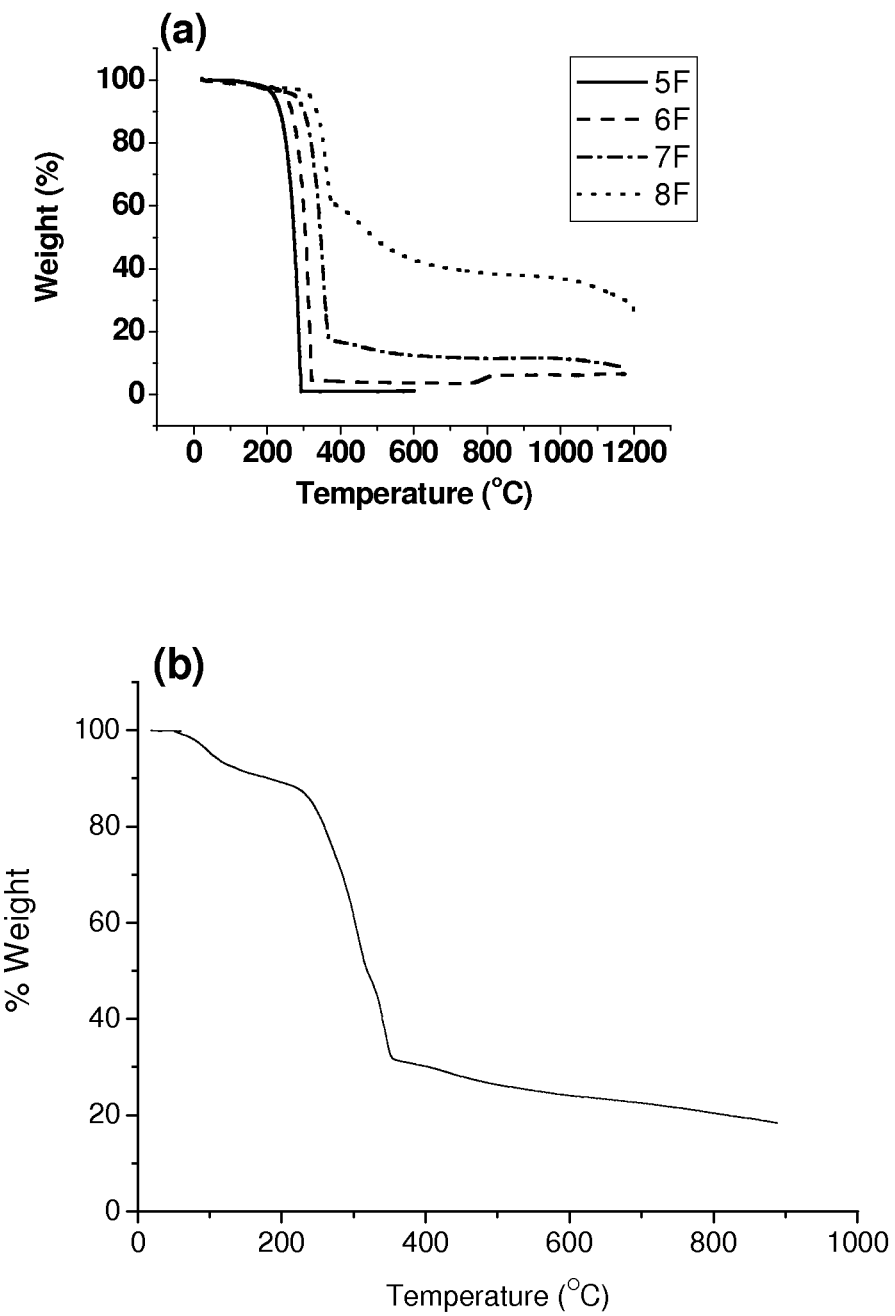
FIG. 3 depicts Thermogravimetric Analysis (TGA) of oligofurans (a) 5F-8F and (b) 9F under $N_2$, rate: 5° C./min.
Figure 4:
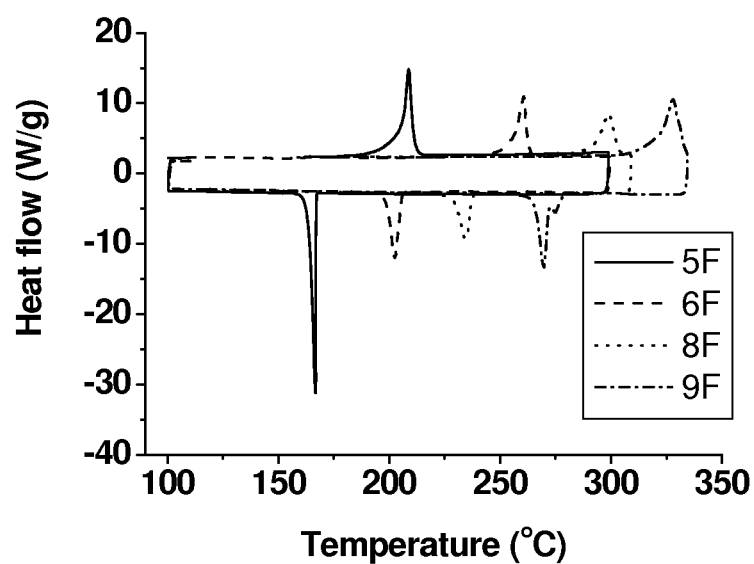
FIG. 4 depicts Differential Scanning calorimetry (DSC) of oligofurans 5F-8F under $N_2$, rate: 10° C./min.
Figure 5:
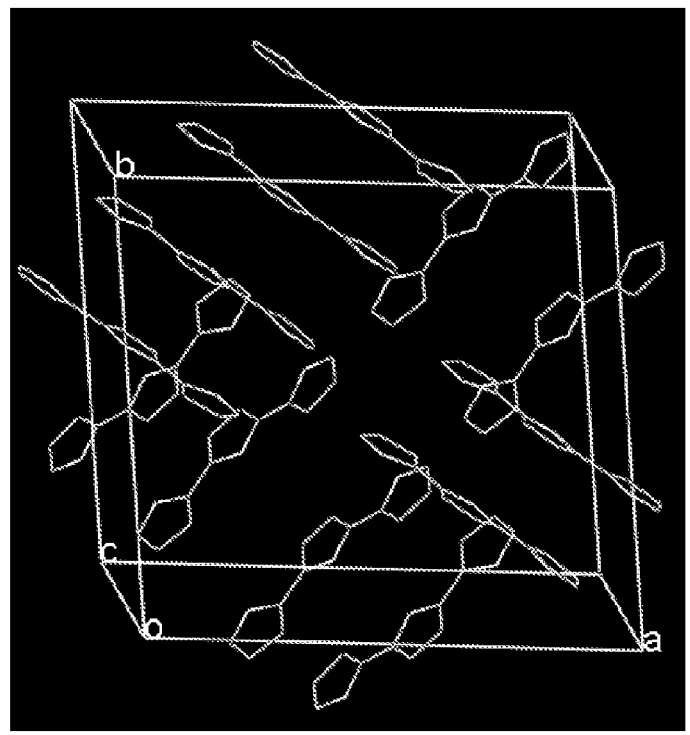
FIG. 5 Crystal packing of α-terfuran (3F). Hydrogen atoms are emitted for clarity.
Figure 6:
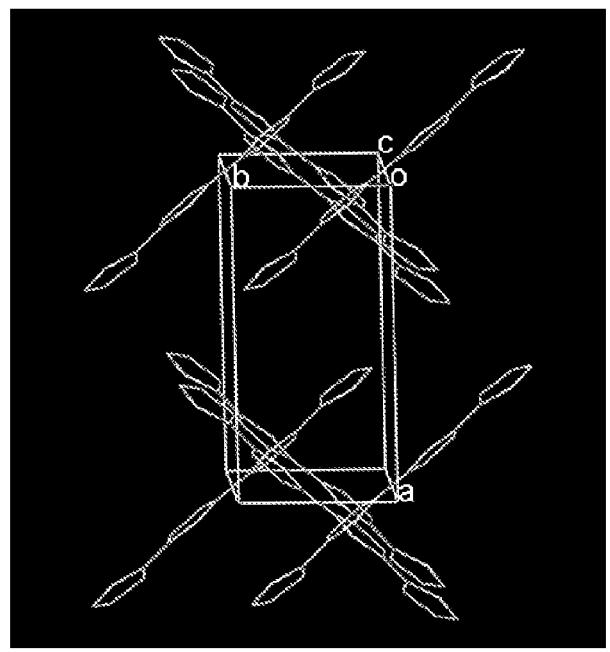
FIG. 6 Crystal packing of α-tetrafuran (4F). Hydrogen atoms are emitted for clarity.

In one embodiment, this invention provides oligofurans and polyfurans which are stable in air. In another embodiment, oligofuran 6F (i.e possessing 6 repeat units) is stable in air in the absent of light, demonstrating decomposition only at 303° C. as presented in FIG. 3. In another embodiment, the oligofurans and polyfurans of this invention are stable in the solid state. X-ray crystallographic analysis revealed a herringbone molecular packing in the solid state tighter than that observed for thiophenes.

In one embodiment, the oligofurans and polyfurans of this invention copolymerise with other polymerisable heterocyclic compounds, or unsaturated systems, such as for example with pyrrole, thiophene, aromatics, alkyne, substituted furan or any combination thereof.

In another embodiment, the alkyne is acetylene, dialkynes, polyalkynes, alkenylalkynes halogen-substituted acetylenes, arylacetylenes, or alkylacetylenes. In another embodiment, the alkyl comprises between 1 to 25 carbon atoms. In another embodiment, the alkyl comprises between 1 to 18 carbon atoms. In another embodiment, the alkyl comprises between 1 to 12 carbon atoms. Examples of alkylacetylenes are propyne, butyne, pentyne, hexyne, heptyne, octyne and decyne. In another embodiment, the arylacetylene is phenylacetylene. In another embodiment the dialkynes and polyalkynes comprise butadiyne, hexadiyne, octadiyne, diethynylbenzene and triethynylbenzene.

In another embodiment, the aromatics are linear fused polynuclear aromatics, such as anthracene, tetracene or pentacene. In another embodiment, the aromatics comprise a phenyl group.

In one embodiment, the oligofuran and polyfuran of this invention is an unsubstituted furan. In another embodiment, the furan itself is substituted. In another embodiment, the substituted furan is N-alkylfuran, N-arylfuran, alkyl-substituted furan, halogenated-furan. In the preparation of the copolymers, the furan can be used alone or mixed with one another, so that the copolymers may contain one or more different furans. In another embodiment, the repeating furan units in the copolymers are essentially based on unsubstituted furan itself.

In one embodiment, this invention provides a process for the preparation of a copolymer comprising furan and the monomer to be polymerized with; comprising reacting 2,5-dibromo-oligofuran of formula I (as described above) with monosubstituted tri-butyltin oligomer. In another embodiment, the reaction between the 2,5-dibromo-oligofuran and monosubstituted tri-butyltin olygomer is in the presence of Pd(PPh$_3$)$_4$. In another embodiment, the monosubstituted tri-butyltin oligomer refers to an oligomer having one end group of hydrogen and the other end group of tri-butyltin. In another embodiment, the oligomer comprises pyrrole, thiophene, aromatics, alkyne, substituted furan or any combination thereof. In another embodiment, the tributyltin end group is in alpha position of pyrrole or thiophene.

In one embodiment, this invention provides a process for the preparation of a copolymer comprising furan and the monomer to be polymerized with; comprising reacting dibromo-oligomer with 2-tributyltin oligofuran of formula II. In another embodiment, the reaction between the dibromo-oligomer and the 2-tributyltin oligofuran (II) is in the presence of Pd (PPh$_3$)$_4$. In another embodiment, the dibromo oligomer refers to an oligomer having two end groups of bromine In another embodiment, the oligomer comprises pyrrole, thiophene, aromatics, alkyne, substituted furan or any combination thereof.

In one embodiment, this invention provides a process for the preparation of copolymers comprising furan and thiophene as monomers. In another embodiment, this invention provides a process for the preparation of copolymers comprising furan and pyrrole as monomers. In another embodiment, this invention provides a process for the preparation of copolymer comprising furan and phenyl as monomers. In another embodiment, this invention provides a process for the preparation of copolymer comprising furan and alkyne as monomers.

In one embodiment, this invention provides a copolymer which is prepared according to the process of this invention comprising furan and substituted furan as monomers. In another embodiment, this invention provides a copolymer which is prepared according to the process of this invention comprising furan or substituted furan with pyrrole or substituted pyrrole as monomers. In another embodiment, this invention provides a copolymer which is prepared according to the process of this invention comprising furan or substituted furan with thiophene or substituted thiophene as monomers. In another embodiment, this invention provides a copolymer which is prepared according to the process of this invention comprising furan or substituted furan with phenyl or substituted phenyl as monomers. In another embodiment, this invention provides a copolymer which is prepared according to the process of this invention comprising furan or substituted furan with alkyne or substituted alkyne as monomers.

In one embodiment, the substituted pyrrole, thiophene, phenyl or alkyne include an alkyl (having 1-18 carbons), phenyl, amine, amide, halogen, hydroxyl, SH, CN, NO$_2$ or COOH groups.

In another embodiment, the proportion of the polyfuran or oligofuran and the monomers to be polymerised can vary within wide limits, depending on the specific type of copolymer, and its intended properties; for example, it can be from 1 to 99% by weight of total weight of the monomers to be polymerised (the percentage by weight is based on the total weight of the monomers to be polymerised). In another embodiment, the ratio of the oligofuran or polyfuran and the monomers to be polymerized is between 20:80 to 90:10.

Methods of Use.

In some embodiments of this invention the polyfurans, oligofurans and copolymers prepared by the processes of this invention can be used for the production of electrodes, catalysts, electrical storage systems, shielding materials, fluorescent markers, dyes, pigments, electrical switches, semiconductor components, electrochromic materials, electromagnetic interference materials, electro-optical devices such as light emitting diodes, field-effect transistors, solar cells, polarizing optical elements and batteries or for the antistatic treatment of plastics.

In one embodiment, this invention provides the use of the oligofuran, polyfuran and copolymer of this invention for imparting antistatic properties on plastic films. In another embodiment, imparting antistatic properties on plastic films comprising a heat treatment of the coated films with mechanical deformation of the films, wherein said films comprise of oligofuran, polyfuran or copolymer of this invention. Simultaneous heat treatment and mechanical deformation of this type takes place in the production of plastic moldings from plastic films by thermoforming the films.

In one embodiment, this invention provides film coatings or layers of the oligofuran, polyfuran or copolymer of this invention in conjunction with a substrate. In another embodiment, non limiting examples of substrate includes a metal foil, a graphite, gold, silicon, glass, a semiconductor, titanium.

In another embodiment, the oligofurans of this invention are highly fluorescent, and can be used as fluorescent materials, markers, field effect transistors embedded in polymer matrices such as PMMA (polymethyl methacrylate).

Figure 10:
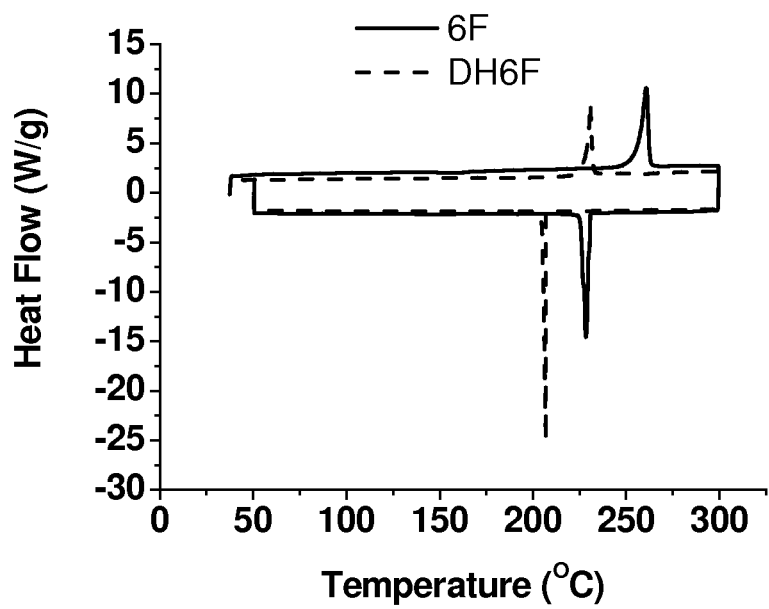
FIG. 10 depicts DSC Differential scanning calorimetry (DSC) of oligofurans 6F and DH-6F under $N_2$, rate: 5° C./min.
Figure 11:
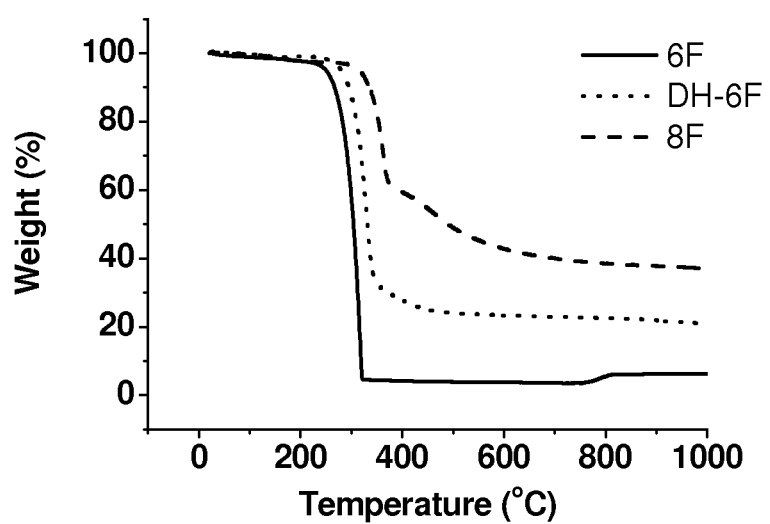
FIG. 11 depicts thermogravimetric analysis (TGA) of oligofurans 6F, 8F and DH-6F under $N_2$. Rate: 5° C./min.
Figure 12:
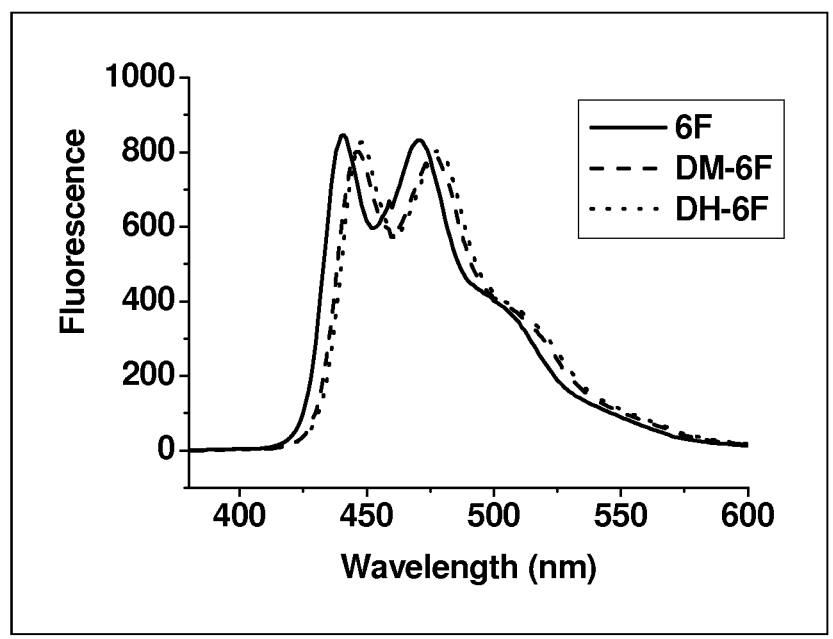
FIG. 12 depicts fluorescence spectra of 6F, DM-6F (dimethyl-sexifuran) and DH-6F (dihexyl-sexifuran).

In one embodiment, the oligomers of this invention are fluorescent. In another embodiment, oligofuran IV-B (DH-6F) is fluorescent, with quantum yield of 72%, and with a melting temperature lower than that of 6F (231° C. and 260° C., respectively, see FIG. 10) for DSC traces). In another embodiment, the oligofuran of this invention are thermally stable. In another embodiment, thermogravimetric analysis (TGA) for the oligofurans of this invention are thermally stable, with sublimation occurs prior to decomposition (FIG. 11).

In one embodiment, the end substitution with alkyl chains gives the molecules liquid-crystalline-like properties, which increases the ordering and enhances the charge mobility of the resulting evaporated films. In another embodiment, elongation of the chain length (i.e increase in number of furan units) or introduction of long alkyl chains leads to decrease of the HUMO-LUMO gap and leads to increase in charge carrier mobility.

In one embodiment, the present invention can further include a method of using oligofuran or polyfuran structural modification to provide, p-type conductivity In one embodiment, the present invention can further include a method of using oligofuran or polyfuran structural modification to provide, n-type conductivity. Such a method includes (1) preparing a elongated oligofuran or polyfuran; (2) providing the oligofuran a structural modification sufficient to promote n-type conductivity, such a modification including but not limited to alkyl, fluoroalkyl substitution, fluorine substitution, fluoroaryl insertion, heterocycle insertion and combinations thereof. Alternatively, various synthetic techniques, depending upon the desired modification, can be made subsequent thereto. Such modifications can provide a wide variety of oligofuran compositions, such compositions including but not limited to those embodiments discussed above.

In another embodiment, the oligomers of this invention is deposited on the substrate by spin casting, drop casting, spraying, knife coating, brushing, subliming or printing.

In one embodiment, to increase or improve the electrical conductivity of the oligofuran, polyfuran or copolymer prepared according to the invention, dopants are added.

In one embodiment, the oligofuran, polyfuran or copolymer of this invention comprise a dopant. In another embodiment, the dopant is p-type. In another embodiment, the p-type dopant is $Br_3^-$, $I_3^-$, $AsF_6^-$, $ClO_4^-$, $BF_4^-$ or $FeCl_4^-$. In another embodiment, the dopant is n-type. In another embodiment, the n-type dopant is $Li^+$, $Na^+$ or $K^+$.

In one embodiment, conductive polyfuran/oligofuran/copolymer films having holes (p-doped) can be formed via conventional p-dopants which include halogen atoms, e.g., $I_2$, $Cl_2$, $Br_2$, ICl, $ICl_3$, IBr and IF, Lewis acids, e.g., $PF_5$, $AsF_5$, $SbF_5$, $BF_3$, $BCl_3$, $SbCl_5$, $BBr_3$ and $SO_3$, protonic acids, organic acids, or amino acids, e.g., HF, HCl, $HNO_3$, $H_2SO_4$, $HClO_4$, $FSO_3H$ and $ClSO_3H$, transition metal compounds, e.g., $FeCl_3$, $Fe(OCl)_3$, $Fe(ClO_4)_3$, $Fe(CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnX_3$ wherein Ln is a lanthanoid and X is an anion, e.g., $Cl^-$, $Br^-$, $I^-$, $I_3^-$, $HSO_4^-$, $SO_4^{2-}$, $NO_3^-$, $ClO_4^-$, $BF_4^-$, $B_{12}F_{12}^{2-}$, $PF_6^-$, $AsF_6^-$, $SbF_6^-$, $FeCl_4^-$, $Fe(CN)_6^{3-}$, and anions of various sulfonic acids, such as aryl-$SO_3^-$. Also, $O_2$, as well as $O_3$, may be used. Conductive polymeric films employing electrons as carriers as in n-doped polymeric films utilize conventional n-dopants which include the alkali metals (e.g., Li, Na, K, Rb, and Cs), alkaline-earth metals e.g., Ca, Sr, and Ba.

In one embodiment, the polyfuran/oligofuran/copolymer of this invention may be doped with conventional p- and n-type dopants post polymerization of the respective monomers. The doping process typically involves treatment of the film material with an oxidizing or reducing agent in a redox reaction to form delocalized ionic centers in the material, with the corresponding counterions derived from the applied dopants. Doping methods comprise for example exposure to a doping vapor in the atmospheric or at a reduced pressure, electrochemical doping in a solution containing a dopant, bringing the dopant in contact with the polymer to be thermally diffused, and ion-implantantion of the dopant into the semiconductor material.

The term "dopant" refers, in one embodiment to a substance which is added to a polyfuran/copolymer in small quantities in order to cause the mixture of polyfuran/copolymer and dopant to be electrically conductive. However, though these polyfuran/copolymer are electrically conductive without a dopant, the magnitude of the conductivity can be increased by adding a dopant material.

In one embodiment, the oligofuran, polyfuran and copolymer of this invention layers and/or composites for thin film deposition are useful in conjunction with the fabrication of thin film transistors and related devices as can be incorporated into an integrated circuit.

In one embodiment, this invention provides a use of the oligofuran, polyfuran or copolymer of this invention as a field-effect active layer in a semiconductor device which is a field -effect transistor. By determining current voltage characteristics at various gate voltages a field -effect is observed. A typical value of the field-effect charge-carrier mobility is approximately $10^{-0}$-$10^{-6}$ cm$^2$/Vs) at a bulk conductivity. These values are typical of amorphous semiconducting polymers processed from solution. A good field-effect transistor combines a high mobility with a low bulk conductivity.

In one embodiment, this invention provides a semiconductor device having a semiconducting layer comprising the formation of a layer by drop casting, spin casting, spin spraying, sublimation, knife coating, brushing or printing (such as inkjet printing) using the oligofuran, polyfuran or copolymer of this invention.

Spin-coating is particularly suitable for devices wherein patterning of the electroluminescent material is unnecessary—for example for lighting applications or simple monochrome segmented displays.

Inkjet printing is particularly suitable for high information content displays, in particular full color displays. Inkjet printing of OLEDs is described in, for example, EP 0880303, which is incorporated herein by reference.

In one embodiment, this invention provides a use of the oligofuran, polyfuran or copolymer of this invention as a coating layer of an electrode. The coating thickness of the applied coating after drying is generally 0.1 to 100 μm, depending on the conductivity desired and on the coating transparency desired.

In one embodiment, this invention provides a use oligofuran, polyfuran or copolymer of this invention as electrode material for rechargeable batteries. In another embodiment the oligofuran, polyfuran or copolymer of this invention are stable when used as electrode material for rechargeable batteries having a lower rate of self-discharge and can be re- and discharged (i.e. cyclised) frequently.

In one embodiment, this invention provides an electrochromic device comprising polyfuran or copolymer of this invention.

In one embodiment, the term "electrochromic device" refers to electrolytic cells that change their ability to transmit (or reflect) light in response to a small bias (typically 1-2 V) applied across the two electrodes.

In another embodiment, the electrochromic devices include displays, electronic ink, sensors, sun glasses, traffic signs or memory elements.

In one embodiment, this invention provides an organic light-emitting device, comprising: a first electrode; a second electrode; an emitting layer interposed between the first electrode and the second electrode; and at least one of a hole transporting layer and a hole injecting layer interposed between the emitting layer and the first electrode, said at least one of the hole transporting layer and the hole injecting layer obtained from a said conducting polymer. In another embodiment the layers are comprised of the polyfuran/oligofuran/copolymer of the invention.

In one embodiment, there is provided an electrical device, for example, an opto-electronic device, comprising a conductive polyfuran/oligofuran/copolymer of this invention as a charge injecting layer in light emitting devices; as a component in electrochromic displays and as electrodes in field-effect transistors and as photovoltaic cells as the alternative for ITO.

In one embodiment, there is provided an electrical device, for example, an opto-electronic device, comprising a conductive polyfuran/copolymer of this invention. In another embodiment, the electrical device comprises an anode, a cathode, and an organic semi-conductive layer between the anode and cathode. The conductive polyfuran/copolymer may be provided in a layer between the anode and cathode. When the conductive polyfuran/copolymer is used as a hole injection material, the layer comprising the conductive polymer is preferably located between the anode and the organic semi-conductive layer. When the conductive polymer is used as an electron transport material, the layer comprising the conductive polymer is preferably located between the cathode and the organic semi-conductive layer or in the organic semi-conductive layer. The organic semi-conductive layer preferably is light-emissive. The anode preferably comprises indium-tin-oxide (ITO).

In another embodiment, the devices of this invention comprising the polyfuran, oligofuran or copolymer of this invention can be used in, e.g. imaging and electronics applications. In another embodiment, the devices can be used as a field effect transistor, light emitting diode, light emitting transistors, photovoltaic cell, or as display backplanes.

A Light Emitting Transistor (LET) is a form of transistor that emits light. Such a transistor has potential for digital displays and on-chip optical interconnects. LET is a new light-emission concept, providing planar light sources that can be easily integrated in substrates like silicon, glass, paper using standard microelectronic techniques. A transistor that emits light and is made from organic materials could lead to cheaper digital displays and fast-switching light sources on computer chips. A transistor-based light source would switch much faster than a diode, and because of its planar design it could be more easily integrated onto computer chips, providing faster data transmission across chips than copper wire. The key to higher efficiency is a three-layer structure, with thin films stacked on top of one another. Current flows horizontally through the top and bottom layers one carrying electrons and the other holes while carriers that wander into the central layer recombine and emit photons. Because they're segregated into their own layer of material, the recombined carriers, known as singlets, don't run into other carriers, and their energy states change to the point where they won't emit photons. Such quenching is one of the major limitations of OLED efficiency.

In one embodiment, this invention is directed to a field effect transistor (FET) device, comprising: (i) a gate electrode; (ii) a source electrode and a drain electrode; (iii) dielectric layer on top of the gate electrode and an oligofuran or polyfuran of this invention between said source and drain electrodes and in electrical contact therewith. In another embodiment, the FET further comprising a substrate with the oligofuran or polyfuran of this invention as a thin film thereon. In another embodiment, the transistor is a junction field effect transistor. In another embodiment, the gate electrode is in electrical contact with a p-type oligofuran/polyfuran organic semiconductor. In another embodiment, the oligofuran or polyfuran is n-type semiconducting. In another embodiment, the oligofuran or polyfuran is p-type semiconducting.

In one embodiment, this invention is directed to a light effect transistor (LET) device, comprising: (i) a gate electrode; (ii) a source electrode and a drain electrode; (iii) dielectric layer on top of the gate electrode and an oligofuran of this invention between said source and drain electrodes and in electrical contact therewith. In another embodiment, the LET further comprising a substrate with the oligofuran of this invention as a thin film thereon. In another embodiment, the gate electrode is in electrical contact with a p-type oligofuran organic semiconductor. In another embodiment, the oligofuran is n-type semiconducting. In another embodiment, the oligofuran is p-type semiconducting.

In one embodiment, this invention is directed to a complementary logic circuit, an active matrix display, an active matrix LED display containing organic transistor devices of this invention.

The organic semi-conductive layer may comprise one or more of a hole transporter, an electron transporter and a light emissive material. One or more further organic semi-conductive layers may be provided between the anode and cathode. One or both of the anode and cathode independently may comprise the conductive polymer composition.

In one embodiment, if multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer. Alternatively, one layer is preferably formed by deposition from solution followed by heat treatment in order to render it substantially insoluble in the solvent used for deposition for a subsequent layer. In this way, cross-linking may be avoided.

Without further elaboration, it is believed that one skilled in the art can, using the preceding description, utilize the present invention to its fullest extent. The following examples and preferred specific embodiments are, therefore, to be construed as merely illustrative, and not limitative of the remainder of the disclosure in any way whatsoever.

EXAMPLES

Preparation of Oligofurans

The oligofurans of this invention were prepared according to the synthetic route as presented in FIG. 1.

General Information $^1$H-NMR spectra were recorded on a 300 MHz spectrometer (Brücker) as a solution in $^2$H-Chloroform with tetramethylsilane (TMS) as the external standard. Chemical shifts are expressed in δ unit. 13C NMR spectra were recorded on 62.50 MHz spectrometer (Brücker) as a solution in $^2$H-Chloroform. UV-VIS absorption measurements were made on a Cary-50 spectrometer (Varian). Steady state fluorescence measurements were performed on a Cary Eclipse fluorimeter (Varian) with excitation/emission geometry at right angles. Fluorescence quantum yields were determined using a standard procedure (Lakowicz, J. R., *Principles of Fluorescence spectroscopy*. 2nd ed.; Kluwer Academic/Plenum: New York, 1999; which is incorporated herein by reference). Quaterfuran in dioxane ($\lambda_{abs}$=364 nm, $\lambda_{em}$=393,418 nm, Φ=0.82) was used as a fluorescence reference (de Melo, J. S.; Elisei, F.; Gartner, C.; Aloisi, G. G.; Becker, R. S. *J. Phys. Chem. A* 2000, 104, 6907; which is incorporated herein by reference). Quantum yield measurements were made using four excitation wavelengths, the quantum yields were averaged over 20 measurements, and the errors were estimated to be less than 5%. Propylene carbonate containing 0.1M tetra-n-butylammonium tetrafluoroborate (TBABF$_4$) was used as a solvent. Ferrocene/ferrocenium redox couple (Fc/Fc$^+$, 0.475 V vs SCE in CH$_2$Cl$_2$) was used as an internal reference for all measurements. All electrochemical measurements were performed under dry nitrogen atmosphere. Dry anhydrous propylene carbonate (PC) was purchased from Sigma-Aldrich and used as it is. tetra-n-butylammonium tetrafluoroborate (TBABF$_4$) Fluka) was dried under vacuum. Ferrocene powder (Fluka) was used to establish an electrochemical reference. Ag/AgCl wire was prepared by dipping silver wire in a solution of FeCl$_3$ and HCl.

Example 1

Preparation of Tributylstannyl-Bifuran and Trifuran Intermediates

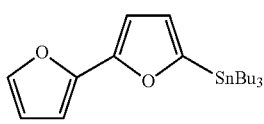

1

2-(tributylstannyl)bifuran (1) A solution of n-BuLi (7.7 mL, of 2.5M in hexanes, 19.2 mmol, 1.3 equivalents) was added dropwise to a solution of bifuran (2 g, 14.9 mmol) in dry THF (100 mL) at −78° C. under N$_2$. The mixture was allowed to come to room temperature and stirred for 1 h. To the white suspension was added dropwise Bu$_3$SnCl (4 mL,  14.9 mmol) at 0° C. and the reaction was allowed to reach room temperature and stirred for 2 h. The mixture was extracted with hexane, dried (MgSO$_4$) and evaporated. Separation by chromatography using bacified silica (Et$_3$N) and hexane gave 1 (3.8 g, 60% yield) as a colorless oil. $^1$H NMR (300 MHz, CDCl$_3$): δ 0.85-0.91 (t, J=7.3 Hz, 9H), 1.03-1.13 (m, 6H), 1.26-1.39 (m, 6H), 1.48-1.63 (m, 6H), 6.40-6.42 (m, 1H), 6.50 (d, J=3.3 Hz, 1H), 6.57 (dd, J=3.3, 6.0 Hz, 2H), 7.34 (dd, J=0.7, 1.8 Hz, 1H) ppm. $^{13}$C NMR (300 MHz, CDCl$_3$): δ 10.2, 13.7, 27.2, 28.9, 104.6, 105.0, 111.3, 123.0, 141.4, 147.5, 151.0, 160.9 ppm

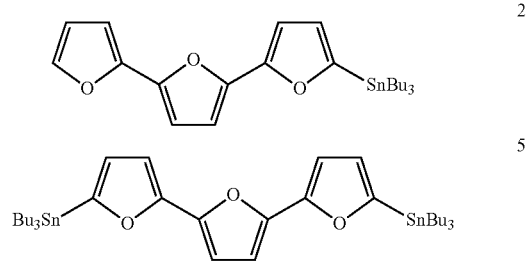

2-(tributylstannyl)terfuran (2) and 5,5"-Bis(tributylstannyl) 2,2':5',2"-terfuran (5) A 2.5M solution of n-BuLi in hexanes (3.2 mL, 8 mmol, 1.6 equivalents) was added dropwise to a solution of terfuran (1 g, 5 mmol) in dry THF (50 mL) at −78° C. under N$_2$. The mixture was allowed to come to room temperature and stirred for 30 min. To the white suspension was added dropwise trimethyltin chloride (1.5 mL, 5.5 mmol) at 0° C. and the reaction was allowed to reach room temperature and stirred for 2 h. The mixture was extracted with hexane, dried (MgSO$_4$) and evaporated. Separation using bacified silica (Net$_3$) and hexane gave 3 (1.05 g, 27% yield), 2 (890 mg, 48% yield) and starting material (110 mg, 11% yield).

2-(tributylstannyl)terfuran (2) $^1$H NMR (300 MHz, CDCl$_3$): δ 0.83-0.90 (t, J=7.3 Hz, 9H), 1.03-1.08 (m, 6H), 1.22-1.38 (dq, J=14.3, 7.2 Hz, 6H), 1.49-1.59 (m, 6H), 6.41-6.43 (dd, J=3.4, 1.8 Hz, 1H), 6.52-6.60 (m, 5H), 7.37 (d, J=1.2 Hz, 1H) ppm. $^{13}$C NMR (300 MHz, CDCl$_3$): δ 10.3, 13.7, 27.2, 28.9, 105.1, 105.4, 106.5, 107.0, 111.4, 123.1, 141.8, 145.4, 146.5, 146.6, 150.6, 161.4 ppm. HRMS (FD): m/z calcd for C$_{24}$H$_{34}$O$_3$Sn: 490.1535. Found 490.1534.

5,5"-Bis(tributylstannyl) 2,2':5',2"-terfuran (5) $^1$H NMR (300 MHz, CDCl$_3$): δ 0.82-0.90 (t, J=7.2 Hz, 18H), 1.01-1.11 (m, 12H), 1.23-1.37 (dq, J=7.2, 14.2 Hz, 12H), 1.48-1.60 (m, 12H), 6.53 (s, 2H), 6.54-6.58 (q, J=3.2 Hz, 4H) ppm. $^{13}$C NMR (300 MHz, CDCl$_3$): δ 10.3, 13.7, 27.2, 28.9, 105.1, 106.5, 123.1, 146.3, 150.8, 161.1 ppm. HRMS (FD): m/z calcd for C$_{36}$H$_{60}$O$_3$Sn$_2$: 778.2595. Found 778.2599.

Example 2

Preparation of Oligofuran (4F)

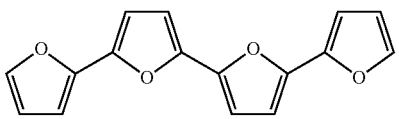

4F

α-quaterfuran (4F) Pd(PPh$_3$)$_4$ (60 mg, 0.05 mmol, 5% mol) was added to 2,5'-(dibromo)bisfuran (289 mg, 1 mmol) and 2-tributyltinfuran (790 mg, 2.2 mmol) in dry toluene (20 mL), and the mixture was refluxed under N$_2$ for 5 h. The mixture was then cooled, evaporated and extracted with dichloromethane. The organic extract was dried (MgSO$_4$), evaporated, and the product was separated over a basified silica (NEt$_3$) column, using hexane as eluent (R$_f$=0.2) to yield white, crystalline product. Characterization of 4F was described elsewhere (Kauffmann et al., *Chemische Berichte* 114, (11), 3667-73 (1981)).

Example 3

Preparation of Oligofuran 5F

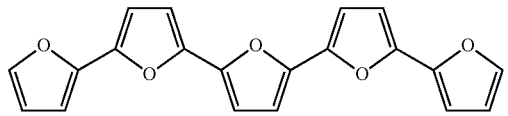

5F

α-pentafuran (5F) Pd(PPh$_3$)$_4$ (350 mg, 0.3 mmol, 10% mol) was added to 2,5"-(dibromo)terfuran (600 mg, 1.39 mmol) and 2-tributyltinfuran (1.2 g, 2.80 mmol) in dry toluene (150 mL), and the mixture was refluxed under N$_2$ for 5 h. The mixture was then cooled, evaporated to approximately 50 mL, and filtered. The filtrate was sublimed under reduced pressure (10$^{-5}$ bar) at 165° C. to give 150 mg of 5F (32% yield), as bright yellow powder. $^1$H NMR (300 MHz, CDCl$_3$): 6.43-6.45 (dd, J=3.4, 1.8 Hz, 2H), 6.58-6.65 (m, 8H), 7.39-7.40 (m, 2H) ppm. $^{13}$C NMR (300 MHz, CDCl$_3$): δ 105.6, 107.1, 107.3, 107.4, 111.5, 142.1, 145.3, 145.5, 146.0, 146.2 ppm. m.p. 208.7° C., HRMS (FD): m/z calcd for C$_{24}$H$_{14}$O$_6$: 332.0685. Found 332.0681. Anal. calcd. for C$_{20}$H$_{12}$O$_5$: C, 72.29; H, 3.64. Found: C, 72.42; H, 3.74.

Example 4

Preparation of Oligofuran 6F

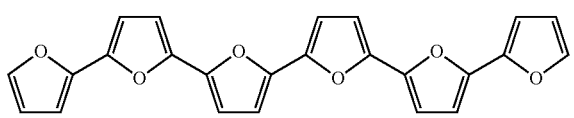

6F

α-sexifuran (6F) Pd(PPh$_3$)$_4$ (600 mg, 0.5 mmol, 10% mol) was added to 2,5'-(dibromo)bisfuran (681 mg, 2.35 mmol) and 2-(tributyltin)bisfuran (1) (2.1 g, 4.95 mmol) in dry toluene (200 mL), and the mixture was refluxed under N2 for 5 h. The mixture was then cooled, evaporated to approximately 50 mL, and filtered. The filtrate was sublimed under reduced pressure (10$^{-5}$ bar) at 190-200° C. to give 315 mg of 6F (34% yield), as bright yellow powder. $^1$H NMR (300 MHz, CDCl$_3$): δ 6.43-6.45 (m, 2H), 6.58-6.66 (m, 10H), 7.38-7.40 (d, 1.4 Hz, 2H) ppm. m.p. 260.5° C., HRMS (FD): m/z calcd for C$_{24}$H$_{14}$O$_6$: 398.0790. Found 398.0787. Anal. calcd. for C$_{24}$H$_{14}$O$_6$: C, 72.36; H, 3.54. Found: C, 72.65; H, 3.58.

Example 5

Preparation of Oligofuran 7F

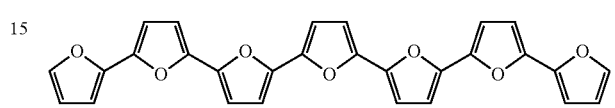

7F

α-heptafuran (7F) Pd(PPh$_3$)$_4$ (350 mg, 0.3 mmol, 10% mol) was added to 2,5'(dibromo)terfuran (500 mg, 1.4 mmol) and 2-(tributyltin)bifuran (1) (1.2 g, 2.8 mmol) in dry toluene (250 mL), and the mixture was refluxed under N2 for 5 h. The mixture was then cooled, evaporated to approximately 50 mL, and filtered. The filtrate was sublimed under reduced pressure (10$^{-5}$ bar) at 240° C. to give 315 mg of 6F (14% yield), as bright orange powder. m.p. 298.8° C., HRMS (FD): m/z calcd for C$_{28}$H$_{16}$O$_7$: 464.0896. Found: 464.0902. Anal. calcd. for C$_{28}$H$_{16}$O$_7$: C, 72.41; H, 3.47. Found: C, 72.12; H, 3.52

Example 6

Preparation of Oligofuran 8F

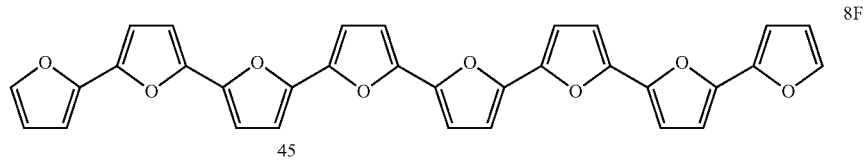

8F

α-octafuran (8F) Pd(PPh$_3$)$_4$ (305 mg, 0.3 mmol, 10% mol) was added to 2,5'-(dibromo)bisfuran (355 mg, 1.2 mmol) and 2-(tributyltin)terfuran (2) (1.2 g, 2.4 mmol) in dry toluene (250 mL), and the mixture was refluxed under N2 for 5 h. The mixture was then cooled, evaporated to approximately 50 mL, and filtered. The filtrate was sublimed under reduced pressure (10$^{-5}$ bar) at 250° C. to give 315 mg of 6F (16% yield), as bright orange powder. m.p. 327.9° C., HRMS (FD): m/z calcd for C$_{32}$H$_{18}$O$_8$: 530.1002. Found 530.1004.

Example 7

Preparation of Oligofuran 9F

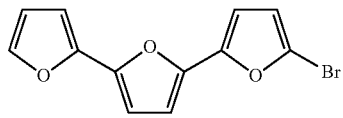

6

5-bromo-2,2':5',2"-terfuran (6) Into an ice bath cooled solution of terfuran (265 mg, 1.3 mmol) in benzene (60 mL) was added N-bromosuccinimide (NBS, 211 mg, 1.2 mmol), and the mixture was stirred for 1 h in the dark. The mixture was then extracted with a saturated solution of sodium hydrogencarbonate, and the organic fraction was passed through a column of basified (NEt$_3$) silica using hexane as eluent. 20 mL of dry toluene was added and hexane was removed by reduced pressure evaporation. The resulting solution was used in the following step without further purification.

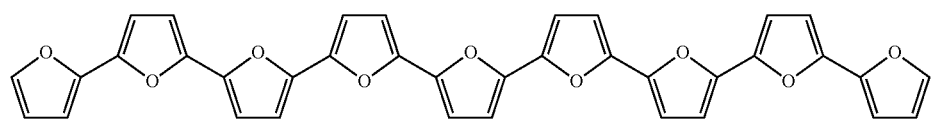

9F

α-nonafuran (2,2':5',2":5",2"':5"',2"":5"",2""':5""',2""":5""",2""""-novifuran) (9F) The above mentioned solution of 2-bromoterfuran (6) in toluene was added to Pd(PPh$_3$)$_4$ (24 mg, 0.02 mmol, 10% mol) and 5,5"-Bis(tributylstannyl) 2,2':5',2"-terfuran (5) (See Example 1) (80 mg, 0.1 mmol) in dry toluene (100 mL) and the mixture was refluxed under N$_2$ for 12 h. The mixture was then cooled, evaporated to approximately 50 mL, the precipitate was collected by filtration, washed with hexane and sublimed under vacuum (10$^{-2}$ mbar) at 265° C. to give 9F as an orange powder. HRMS (FD): m/z calcd for C$_{36}$H$_{20}$O$_9$: 596.1107. Found 596.1109.

The product can be also separated by Soxlhet extraction, since it is slightly soluble in warm acetone. After 2 h. of Soxlhet with acetone the soluble impurities were removed, a new fraction of acetone was introduced and the product can be seen in the flask as an orange precipitate.

Example 8

Photophysical Properties of the Oligofurans of this Invention

All electrochemical measurements were performed using PAR Potentiostat model 263A in a standard three-electrode, one compartment configuration equipped with Ag/AgCl wire, Pt wire and Pt disk electrode (dia 1.6 mm from BASi), as the pseudo reference, counter electrode and working electrode, respectively. Pt disk electrodes were polished with alumina followed by sonication and further electropolished in 0.5M HClO4 by cycling between −0.23 and 1.25 V vs. a Ag/AgCl saturated NaCl electrode (BASi). The electrolytic medium contained anhydrous propylene carbonate (PC) and 0.1 M tetrabutylamonium tetrafluoroborat (TBABF$_4$) as electrolyte. All electrochemical solutions were purged with dry N$_2$ for 15 minutes at least. Under these conditions, a Fc/Fc+ standard was calibrated to be 0.34 V. Monomer concentration was about 10$^{-2}$ M.

Figure 8:
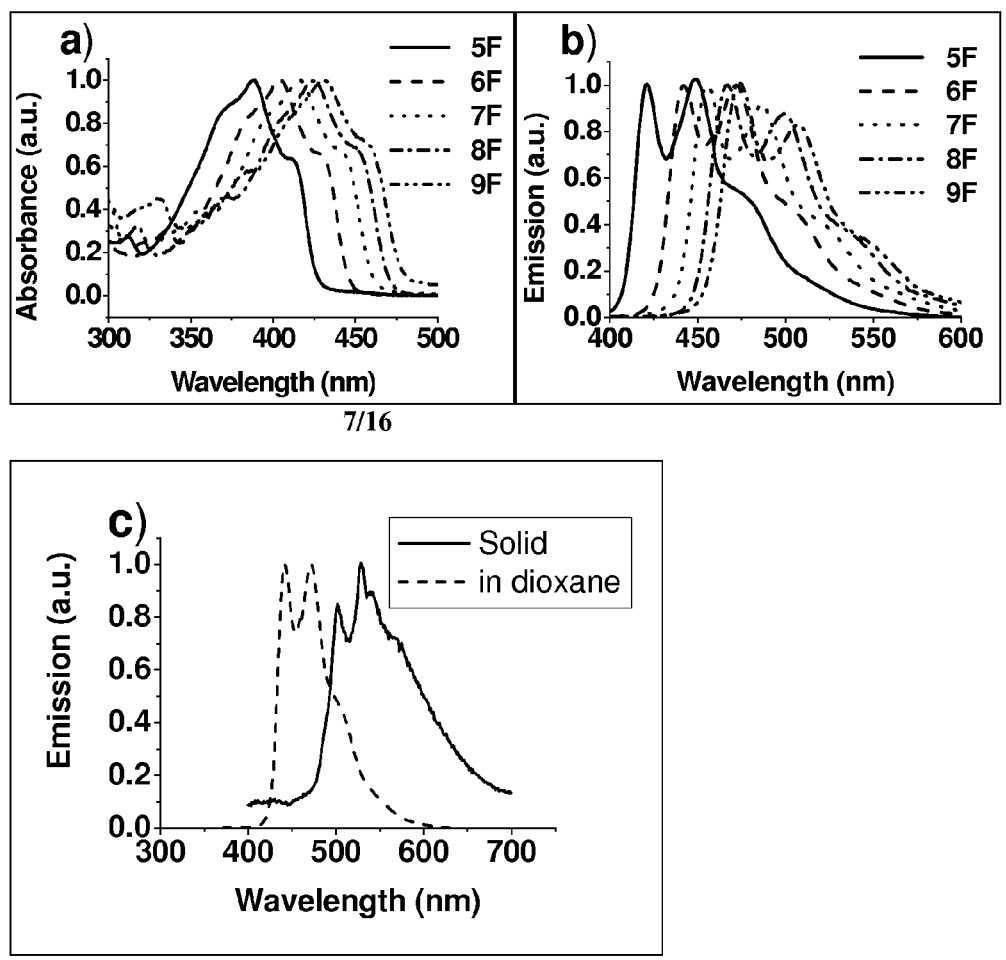
FIG. 8 UV/VIS and fluorescent spectra of oligofurans 5F-9F (i.e 5F refers to α-pentafuran; 6F to α-sexifuran; 7F to α-hepafuran; 8F to α-octafuran and 9F to α-nonafuran. (A) absorbance in dioxane; (B) fluorescence of 5F-9F in dioxane (C) fluorescence spectra of 6F in the solid state (powder) and in solution (dioxane).
Figure 9:
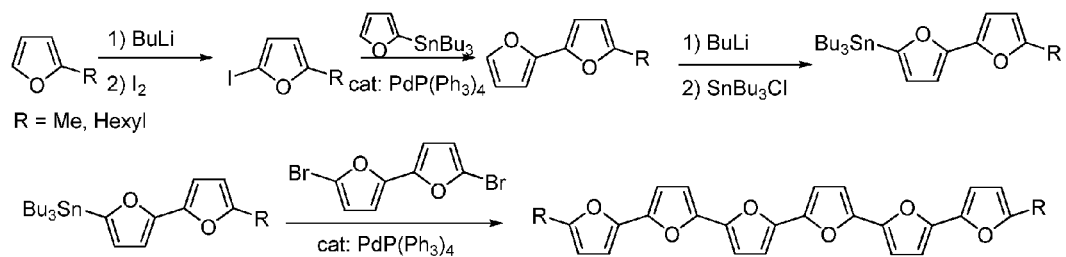
FIG. 9. depicts a synthetic scheme of oligofuran IV-B (DH-6F, dihexyl-6F).

Oligofurans are highly fluorescent, with quantum yield ranging from 58% in 9F to 74% in 5F (Table 1, FIG. 8). The Stokes shift values are around 0.25 eV for 3F-9F, and are substantially smaller than for the corresponding oligothiophenes 3T-6T (around 0.40 eV), indicating that oligofurans are more rigid. The solid state fluorescence of 6F showed peaks that are red shifted 0.35 eV relative to their value in solution (FIG. 8). In addition to the smaller Stokes shift and closer packing mentioned above, the rigidity of oligofurans can be seen from the calculated twisting potentials (FIG. 16). The energy required to twist 6F was significantly greater than for 6T. For example, twisting 6F to a 36° twist angle required 12.5 kcal/mol, while similar twisting in 6T required only 2.3 kcal/mol. The smaller size of oxygen atom compared to sulfur atom which lead to less steric demand in oligofurans compared to oligothiophenes may also contribute to the significant difference in the rigidity. The above findings indicate that, in spite of better solubility, oligofurans are more rigid than oligothiophene.

Table 1, provides the absorption, fluorescence quantum yield and redox properties of the oligofurans of this invention.

TABLE 1

Photophysical and electrochemical data for oligofurans.

| | ε$_{max}$[a] (M$^{-1}$ cm$^{-1}$) | λ$_{abs}$[a] (nm) | λ$_{flu}$[a] (nm) | Φ$_f$[a,b] | E$_{ox}$[c,d] (V) | HOMO[e] (eV) |
|---|---|---|---|---|---|---|
| 5F | 51000 | 388 | 421, 449 | 0.74 (0.36) | 0.71 (0.67) | −4.62 |
| 6F | 53000 | 404 | 442, 472 | 0.69 (0.41) | 0.67 (0.66) | −4.55 |
| 7F | 56000 | 417 | 455, 485 | 0.67 | 0.66 (0.66) | −4.51 |
| 8F | 56000 | 423 | 467, 499 | 0.66 | 0.67 (0.68) | −4.48 |
| 9F | — | 430 | 473, 507 | 0.58 | — | −4.45 |

Figure 15:
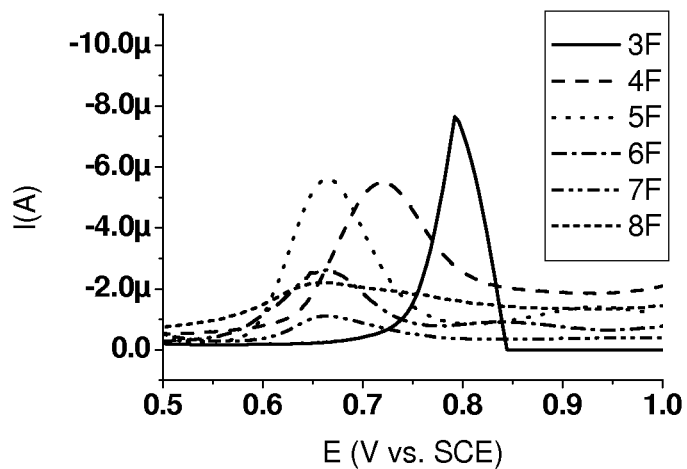
FIG. 15 depicts Differential Pulse Voltammogram (DPV) of oligofurans. Conditions: scan rate, 20 mV s$^{-1}$, 0.1 M $TBABF_4$ in PC reference electrode Ag/AgCl, Fc/Fc$^+$=0.34 V vs. SCE under these conditions.

[a]Measured in dioxane.
[b]Fluorescence quantum yields for the corresponding oligothiophen (nTs) (taken from Becker et al. J. Phys. Chem. 1996, 100, 18683) are given in parentheses.
[c]Oxidation potentials measured in propylene carbonate with 0.1M tetra-n-butylammonium tetrafluoroborate, reference electrode Ag/AgCl, Fc/Fc$^+$ = 0.34 V vs. SCE under these conditions, scan rate: 100 mV/s.
[d]Values in parentheses corresponds to Differential pulse voltammogram (DPV) measurements (FIG. 15).
[e]Calculated values (B3LYP/6-31G(d)).
[f]Data were taken from de Melo, et al. J. Phys. Chem. A 2000, 104, 6907, measured in MeCN.

Example 9

Crystallization and X-Ray Analysis of the Oligofurans of this Invention

General X-ray Procedures:

The X-ray diffraction data were collected on a Nonius KappaCCD diffractometer, MoKα (λ=0.71073 Å), graphite monochromator, T=100(2)K. The data were processed with Denzo-Scalepack. The structures were refined by full matrix least-squares based on F2 with SHELXL-97.

X-ray Structural Analysis of α-sexifuran (6F) Compound 6F was crystallized from a heptane to give pale yellow crystals (plates). Crystal data: C$_{24}$H$_{14}$O$_6$, 0.10×0.10×0.01 mm$^3$, Monoclinic, P2(1)/c, a=19.4403(16) Å, b=5.2922(4) Å, c=8.9457(O) Å, α=90 β=99.719(5) γ=90 from 18 degrees of data, Z=2, Fw=398.35, Dc=1.458 Mg·m$^{-3}$, n=0.106 mm$^{-1}$ Data collection and processing: Bruker KappaApexII CCD diffractometer, MoKα (λ, =0.71073 Å), graphite monochromator, MiraCol optics, −23≤h≤23, −6≤k≤6, −6≤l≤10, frame scan width=0.5°, scan speed 1.0° per 160 sec, typical peak mosaicity 0.67°, 6398 reflections collected, 1725 independent reflections (R-int=0.0984). The data were processed with Apex2. Solution and refinement: Structure solved by direct methods with Bruker Auto-Structure. Full matrix least-squares refinement based on F$^2$ with SHELXL-97 136 parameters with 0 restraints, final $R_1=0.0501$ (based on $F^2$) for data with I>2σ(') and $R_1=0.1807$ on 3763 reflections, goodness-of-fit on $F^2=0.925$, largest electron density peak=0.212 e/Å$^3$ and hole −0.257 e/Å$^3$.

X-ray Structural Analysis of α-terfuran (3F) Compound 3F was crystallized from a heptane to give colorless crystals. Crystal data: $C_{12}H_8O_3$, 0.36×0.11×0.08 mm$^3$, Monoclinic, Cc, a=17.982(5) Å, b=16.300(5) Å, c=10.747(2) Å, 13=116.82 (3) from 27 degrees of data, V=2811.2 (15) Å$^3$, Z=12, Fw=200.18, Dc=1.419 Mg·m$^{-3}$, μ=0.103 mm$^{-1}$ Data collection and processing: Nonius KappaCCD diffractometer, MoKα (λ, =0.71073 Å), graphite monochromator, −24≤h≤18, −21≤k≤21, −13≤l≤14, frame scan width=1.0°, scan speed 1.0° per 80 sec, typical peak mosaicity 0.72°, 24341 reflections collected, 7021 independent reflections (R-int=0.0463). The data were processed with Denzo-Scalepack. Solution and refinement: Structure solved by Patterson method with SHELXS-97. Full matrix least-squares refinement based on $F^2$ with SHELXL-97 406 parameters with 2 restraints, final $R_1=0.0403$ (based on $F^2$) for data with I>2σ(I) and $R_1=0.0529$ on 3543 reflections, goodness-of-fit on $F^2=1.016$, largest electron density peak=0.369 e/Å$^3$ and hole −0.222 e/Å$^3$.

X-ray Structural Analysis of α-tetrafuran (4F) Compound 4F was crystallized from a heptane to give colorless crystals. Crystal data: $C_{16}H_{10}O_4$, 0.3×0.1×0.2 mm$^3$, Monoclinic, P2$_1$/c (No. 14), a=11.2338(17) Å, b=5.3584(7) Å, c=10.9863 (16) Å, β=114.828(5) from 20 degrees of data, V=600.20(15) Å$^3$, Z=2, Fw=266.24, Dc=1.473 Mg·m$^{-3}$, μ=0.107 mm$^{-1}$ Data collection and processing: Bruker KappaApexII CCD diffractometer, MoKα (λ, =0.71073 Å), graphite monochromator, MiraCol optics, −12≤h≤12, −5≤k≤5, −12≤l≤12, frame scan width=0.5°, scan speed 1.0° per 140 sec, typical peak mosaicity 0.46°, 5329 reflections collected, 869 independent reflections (R-int=0.0731). The data were processed with Apex2. Solution and refinement: Structure solved by direct methods with SHELXS. Full matrix least-squares refinement based on $F^2$ with SHELXL-97 91 parameters with 0 restraints, final $R_1=0.0428$ (based on $F^2$) for data with I>2σ(I) and $R_1=0.0837$ on 863 reflections, goodness-of-fit on $F^2=1.026$, largest electron density peak=0.191 e/Å$^3$ and hole −0.298 e/Å$^3$.

Example 10

Synthesis of Compound IV-B (dihexyl-6F)

General Information $^1$H and $^{13}$C NMR spectra were recorded in solution on a 300 MHz spectrometer (Brücker) using $^2$H-chloroform as the solvent and tetramethylsilane (TMS) as the external standard. Chemical shifts are expressed in δ unit. High resolution mass spectra were measured on a Waters Micromass GCT$_{13}$Premier.

Synthesis

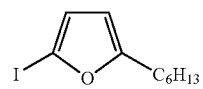

2-hexyl-5-iodofuran. A solution of n-BuLi (24.7 mL, 1.6 M in hexanes, 39.5 mmol, 1.4 equivalents) was added dropwise to a solution of 2-hexylfuran (4.3 g, 28.3 mmol) in dry tetrahydrofuran (THF, 50 mL) at −78° C. under N$_2$. The reaction mixture was warmed to 0° C., stirred for 10 min and cooled again to −78° C. To this solution was added slowly iodine (9.3 g, 36.7 mmol) in 25 mL of THF, and the solution was warmed slowly to 0° C. and stirred for 2 h at 0° C. After addition of 100 mL of water, the solution was extracted with hexane. The organic layer was washed with aqueous Na$_2$S$_2$O$_3$ solution (30 mL) and water, dried over MgSO$_4$, filtered, and concentrated. The crude product was purified by silica gel column chromatography (elution with hexane) to afford 6 g of 2-hexyl-5-iodofuran (76%) as a pale brownish oil. $^1$H NMR (300 MHz, CDCl$_3$): δ6.37 (d, J=3.14 Hz, 1H), 5.88 (d, J=3.16 Hz, 1H), 2.60 (t, J=7.56, 7.56 Hz, 2H), 1.58 (td, J=15.11, 7.66, 7.66 Hz, 2H), 1.24-1.39 (m, 6H), 0.86 (t, J=6.77, 6.77 Hz, 3H) ppm. $^{13}$C NMR (75 MHz, CDCl$_3$): δ 162.3, 120.6, 108.0, 84.3, 31.6, 28.8, 28.3, 27.8, 22.6, 14.1 ppm. HRMS (FD): m/z calcd for $C_{10}H_{15}IO$: 278.0168. Found 278.0172.

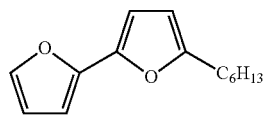

5-hexyl-2,2'-bifuran. Pd(PPh$_3$)$_4$ (1.15 g, 1 mmol, 5% mol) was added to 2-tributyltinfuran (7.05 g, 20 mmol) and 2-hexyl-5-iodofuran (5.5 g, 20 mmol) in dry toluene (150 mL) and the reaction mixture was refluxed under N$_2$ for 5 h. The mixture was then cooled, separated with hexane, the organic layer was dried over MgSO$_4$, filtered, and concentrated. The crude product was purified by silica gel column chromatography (elution with hexane) to afford 3.8 g of 5-hexyl-2,2'-bifuran (88%) as a colorless oil. $^1$H NMR (300 MHz, CDCl$_3$): δ 7.35 (d, J=1.1 Hz, 1H), 6.39-6.45 (m, 3H), 6.00 (d, J=3.2 Hz, 1H), 2.62 (t, J=7.6, 2H), 1.64 (td, J=2H), 1.28-1.34 (m, 6H) 0.87 (t, 3H) ppm. $^{13}$C NMR (75 MHz, CDCl$_3$): δ 156.3, 147.0, 144.8, 141.3, 111.3, 106.5, 105.9, 104.1, 31.6, 28.9, 28.1, 28.0, 22.6, 14.1 ppm. HRMS (FD): m/z calcd for $C_{14}H_{18}O_2$: 218.1307. Found 218.1315.

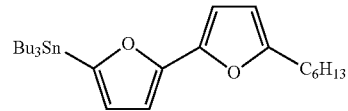

Tributyl(5'-hexyl-[1,2'-bifuran]-5-yl)stannane). A solution of n-BuLi (14.1 mL, 1.6 M in hexanes, 22.5 mmol, 1.3 equivalents) was added dropwise to a solution of 2-hexyl-5-iodofuran (3.8 g, 17.4 mmol) in dry tetrahydrofuran (THF, 100 mL) at −78° C. under N$_2$. The reaction mixture was allowed to reach to room temperature and stirred for 1 h. The resulting mixture was cooled to −78° C., Bu$_3$SnCl (6.1 mL, 22.5 mmol) was added dropwise and the reaction mixture was allowed to reach room temperature and stirred for 2 h. The mixture was quenched with water, extracted with hexane, dried (MgSO$_4$), and evaporated. Flash chromatography on a basified (NEt$_3$) silica, using hexane as eluent gave Tributyl (5'-hexyl-[2,2'-bifuran]-5-yl)stannane) (1.9 g, 20% yield) as a colorless oil. $^1$H NMR (300 MHz, CDCl$_3$): ppm. $^{13}$C NMR (75 MHz, CDCl$_3$): δ 106.1, 155.9, 151.4, 145.7, 122.9, 106.4, 105.4, 104.0, 31.6, 28.9, 28.8, 28.1, 28.0, 27.2 22.6, 14.7, 14.1, 10.2 ppm. HRMS (FD): m/z calcd for $C_{26}H_{44}O_2Sn$: 508.2368. Found 508.2374.

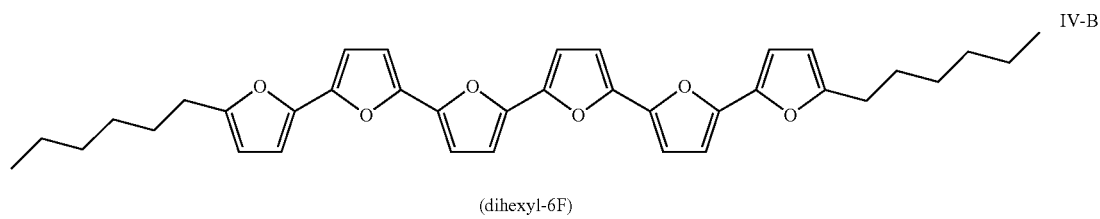 [SMILES: CCCCCCc1ccc(-c2ccc(-c3ccc(-c4ccc(-c5ccc(-c6ccc(CCCCCC)o6)o5)o4)o3)o2)o1]

IV-B (dihexyl-6F)

5,5''''-dihexyl-2,2':5',2'':5'',2''':5''',2'''':5'''',2''''''-sexifuran (DH-6F). Pd(PPh$_3$)$_4$ (115 mg, 0.1 mmol, 5% mol) was added to 2,5'-(dibromo)bisfuran (283 mg, 1 mmol) and Tributyl(5'-hexyl-[2,2'-bifuran]-5-yl)stannane (1 g, 2 mmol) in dry toluene (200 mL) and the reaction mixture was refluxed under N$_2$ for 5 h. The mixture was then cooled, concentrated to approximately 50 mL, the residue was collected by filtration, washed with acetone and sublimed under reduced pressure (10$^{-2}$ mbar) at 190-200° C. to give 190 mg of DH-6F (35% yield) as a bright yellow powder, m.p. 261° C. $^1$H NMR (400 MHz, 1,1,2,2-Tetrachloroethane-d$_2$): δ 6.62-6.67 (m, 4H), 6.52 (d, J=3.54 Hz, 2H), 6.50 (d, J=3.19 Hz, 2H), 6.03 (d, J=3.32 Hz, 2H), 2.64 (t, J=7.51, 7.51 Hz, 4H), 1.59-1.67 (m, 4H), 1.26-1.36 (m, 12H), 0.86 (t, J=7.04 Hz, 6H). $^{13}$C NMR (100 MHz, 1,1,2,2-Tetrachloroethane-d$_2$): δ 156.5, 144.9, 144.3, 143.7, 107.1, 107.0, 106.7, 106.2, 106.1, 105.8, 105.7, 30.9, 28.2, 27.5, 27.3, 21.9, 13.4 ppm. HRMS (FD): m/z calcd for C$_{36}$H$_{38}$O$_6$: 566.2668. Found 566.2674

Example 11

Morphology of Selected Oligofuran Films of this Invention

Methods and Materials

Differential scanning calorimetry (DSC) measurements were performed on a TA Q200 DSC instrument. Elemental analysis was carried out with a FlashEA 1112 Thermo Finnigan CHN elemental analyzer. UV-vis absorption measurements were made on a Cary-50 spectrometer (Varian). Steady state fluorescence measurements were performed on a Cary Eclipse fluorimeter (Varian) with the excitation/emission geometry at right angles. Fluorescence quantum yields were determined using a standard procedure (Lakowicz, J. R., *Principles of Fluorescence spectroscopy.* 2nd ed.; Kluwer Academic/Plenum: New York, 1999). Coumarine 30 in MeCN ($\lambda_{abs}$=403 nm, $\lambda_{em}$=480 nm, $\Phi_f$=0.67) was used as a reference for $\Phi_f$ measurements (Jones, G.; Jackson, W. R.; Choi, C.; Bergmark, W. R. *J. Phys. Chem.* 1985, 89, 294-300).

Quantum yield measurements were made using four excitation wavelengths, the quantum yields were averaged over 20 measurements, and the errors were estimated to be less than 5%. For solid state fluorescence, the compound was measured as powder placed between two quartz slides. Propylene carbonate containing 0.1M tetra-n-butylammonium tetrafluoroborate (TBABF$_4$) was used as a solvent. Ag/AgCl was used as a reference electrode. A ferrocene/ferrocenium redox couple (Fc/Fc$^±$=0.34 V vs. saturated calomel electrode (SCE) in propylene carbonate (PC)) was used as an internal reference for all measurements. All electrochemical measurements were performed under a dry nitrogen atmosphere. Dry anhydrous PC was purchased from Sigma-Aldrich and used as it is. TBABF$_4$ (Fluka) was dried under vacuum. Ferrocene powder (Fluka) was used to establish an electrochemical reference. Ag/AgCl wire was prepared by dipping silver wire in a solution of FeCl$_3$ and HCl. THF and toluene were distilled from sodium/benzophenone under an atmosphere of dry argon prior to use. Columns were prepared with silica gel (60-230 mesh).

Results

Figure 13:
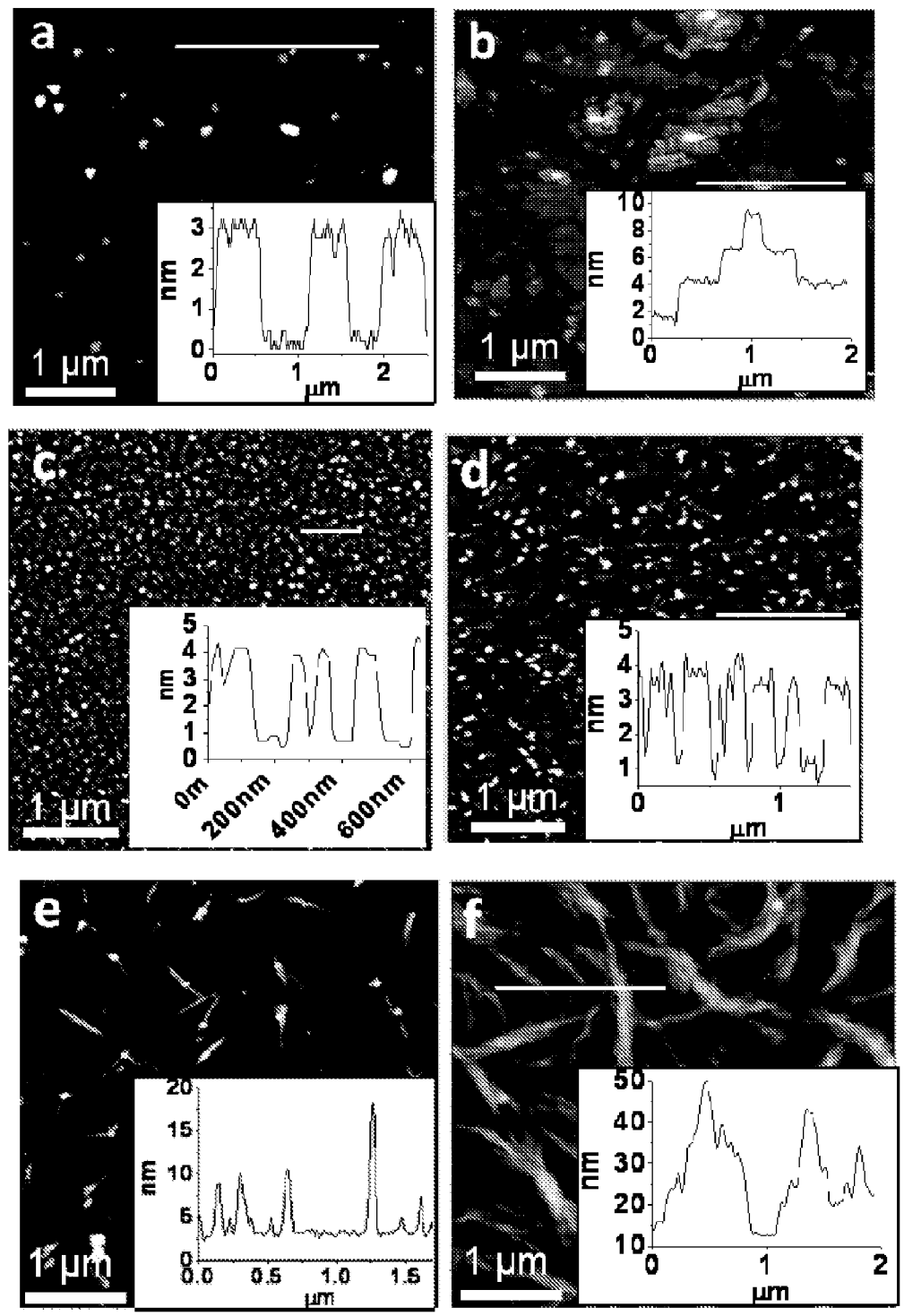
FIG. 13 depicts AFM images and cross section diagrams of (a) DH-6F after deposition times of 20 sec (sub ML regime), (b) DH-6F after 120 sec. deposition (3 layers thickness), (c) to 8F after deposition times of 20 sec and (d) 60 sec, (e) 6F after deposition time of 20 and (f) 60 sec, on Si/$SiO_2$.
Figure 14:
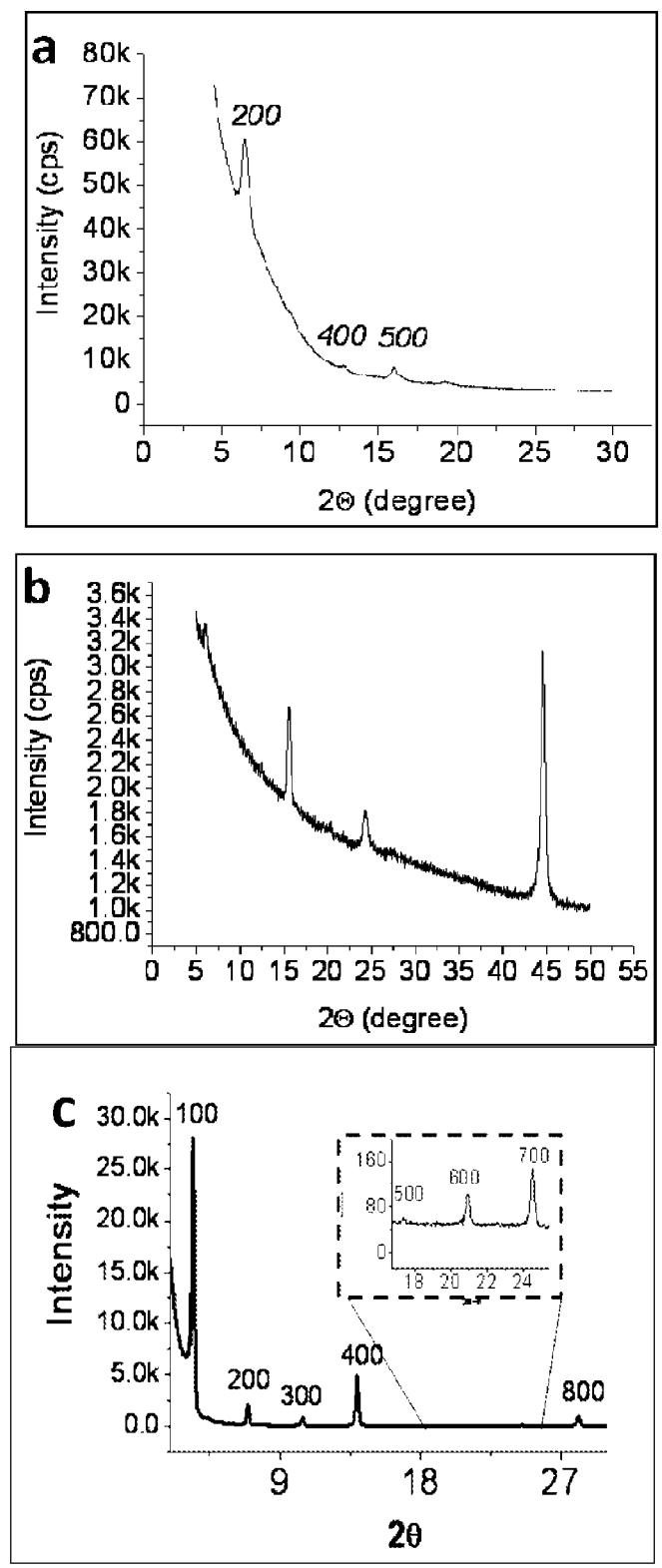
FIG. 14 depicts. XRD patterns for vacuum deposited films of (a) DH-6F (b) 6F and (c) 8F.

The film morphologies of oligofurans vacuum deposited on Si/SiO$_2$ were studied by atomic force microscopy (AFM) and X-ray diffraction (XRD). AFM images of DH6F show a layer-by-layer deposition, with a layer thickness of ~2.8-3.0 nm (FIG. 13 *a*). This is in agreement with the XRD measurements on these films, which reveal only a set of h00 diffraction peaks for DH6F (FIG. 14*a*) with corresponding d-spacing of 2.75 nm. This distance corresponds to the calculated length of DH6F (3.89 nm) radii of methyl group of 0.2 nm) with a tilt angle of 45°. The film growth is continued in a layer-by-layer fashion, at least for the first three monolayers (FIG. 13*b*). For 8F, layer deposition is observed as well, with the thickness of 3 nm, indicating the molecules are aligned normal to the surface (the calculated length is 3.09 nm) (FIG. 13*c,d*). Again, the layer-by-layer deposition is confirmed by XRD which shows a set of h00 peaks (up to eights order), with d-spacing of 2.54 nm (FIG. 14*b*). The morphology of 6F films is very different from that of 8F and DH-6F films. AFM image indicates the formation of 1D 'wires' (FIG. 13*e*), which form bundles at longer deposition times (FIG. 13*f*). The XRD pattern of such film shows no selective alignment of the crystallographic planes of 6F vs the substrate (FIG. 14*c*). Similar results were obtained when the molecules were deposited on OTS- or HMDS-modified Si/SiO$_2$ wafers (HMDS=hexamethyldisilazane).

Example 12

Electrochemistry of Oligofuran of this Invention

Materials and Methods

All electrochemical measurements were performed using PAR Potentiostat model 263A in a standard three-electrode, one compartment configuration equipped with Ag/AgCl wire, Pt wire, and Pt disk electrode (dia 1.6 mm from BASi) as the pseudo reference, counter electrode, and working electrode, respectively. Pt disk electrodes were polished with alumina followed by sonication and further electropolished in 0.5M HClO$_4$ by cycling between −0.23 and 1.25 V vs. Ag/AgCl saturated NaCl electrode (BASi). The electrolytic medium contained anhydrous propylene carbonate (PC) and 0.1 M TBABF$_4$ as electrolyte. All electrochemical solutions were purged with dry N$_2$ for at least 15 minutes. Under these conditions, a Fc/Fc$^+$ standard was calibrated to be 0.34 V. Monomer concentration was about 10$^{-2}$ M.

Results

Figure 2:
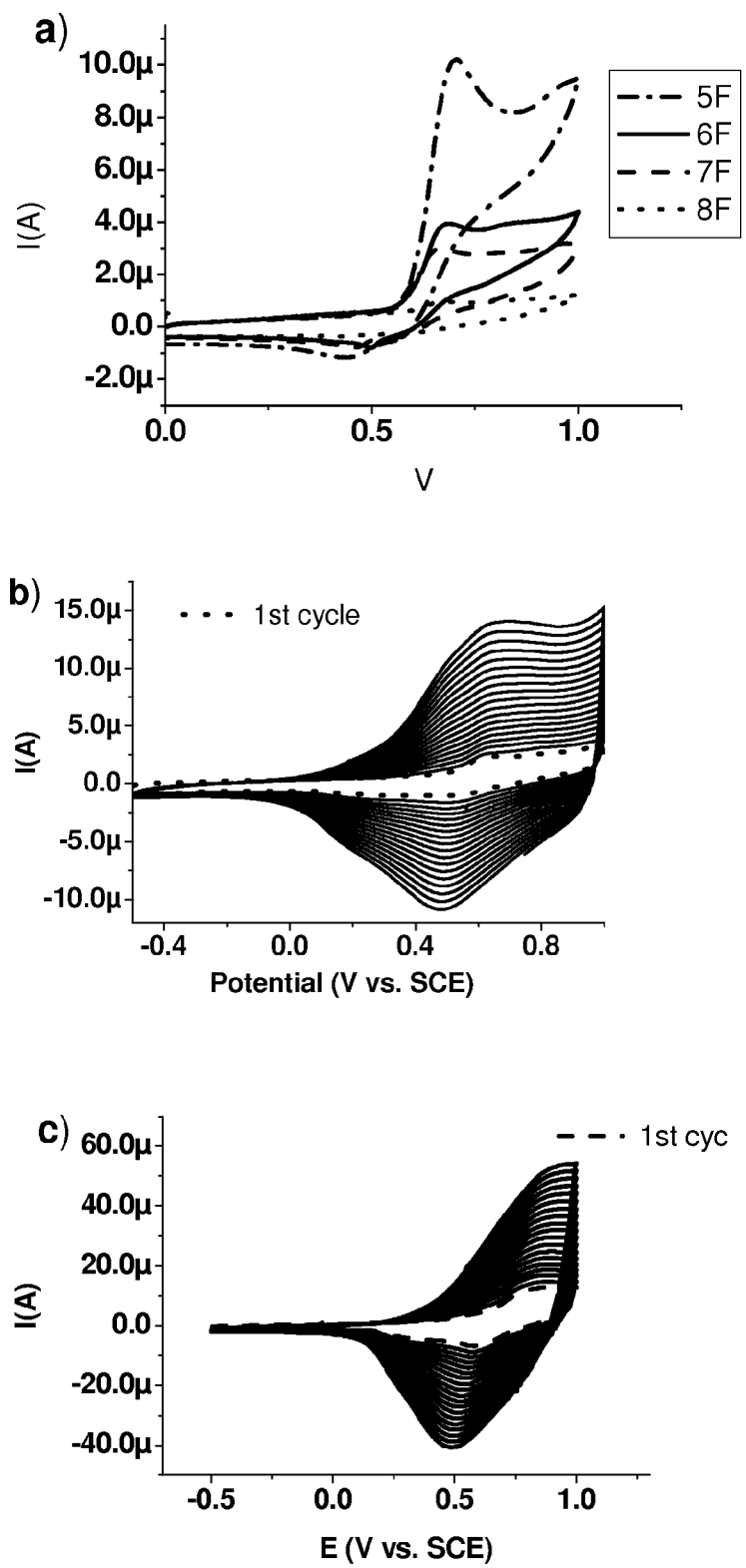
FIG. 2 depicts (a) Cyclic Voltammetry (CV) of oligofurans 5F-8F in propylene carbonate (PC) and 0.1M tetra-n-butylammonium tetrafluoroborate ($TBABF_4$), scan rate: 50 mV/sec; (b) Repetitive CV scans of 6F in 1,2-dichloroethane with 0.1M TBABF, scan rate 100 mV/s, Fc/Fc$^+$=0.34 V vs. SCE under these conditions. (c) Multi-sweep electropolymerization of 6F on a Pt electrode in 1,2-dichloroethane, scan rate, 50 mV s$^{-1}$, 0.1 M $TBABF_4$, reference electrode Ag/AgCl, Fc/Fc$^+$=0.34 V vs. SCE under these conditions

Cyclic voltammetry (CV) of 5F-8F showed an irreversible oxidation peak at 0.71 V for 5F to 0.67 V vs. SCE for 8F (FIG. 2*a* and Table 1 in Example 8, calibrated for Fc/Fc$^+$=0.34 V vs. SCE). This is in agreement with the calculated difference of only 0.14 eV in the HOMO energies of 5F-8F (Table 1). Long oligofurans are significantly more electron rich compared to oligothiophenes, as evident from their relatively low oxidation potentials. For comparison, the oxidation potentials of 3T and 4T are 1.16 V and 1.14 V, respectively, under similar conditions. In the cases of 5F-7F, smooth polymer growth is observed during repetitive cycling (FIG. 2*b*). The color of the formed film is yellowish orange in the neutral state which changes to green upon doping.

Example 13

Synthesis of DPFB-6F Oligofuran

Figure 17:
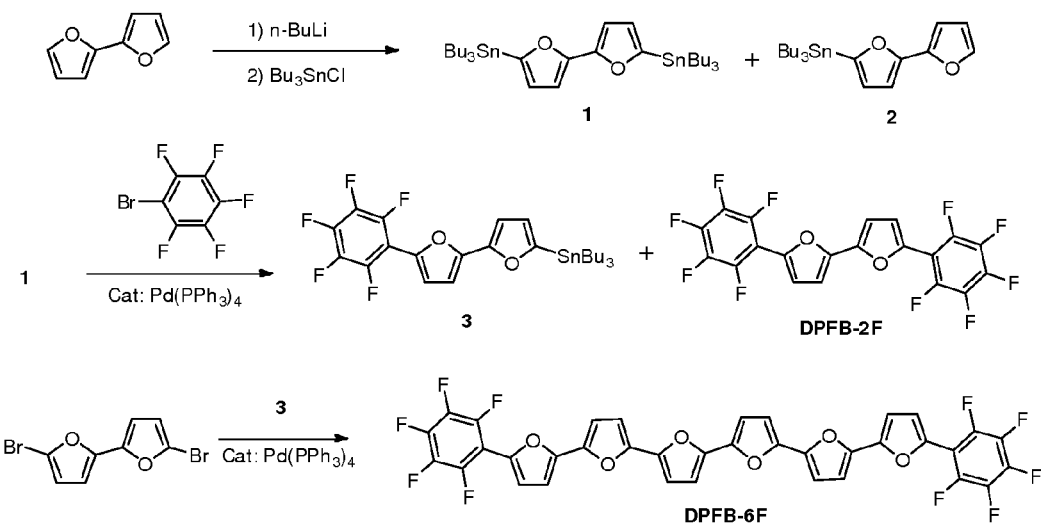
FIG. 17 depicts synthetic route to DPFB-6F and DPFB-2F oligofurans.

The synthetic scheme for the preparation of DPFB-6F oligofuran is depicted in FIG. 17.

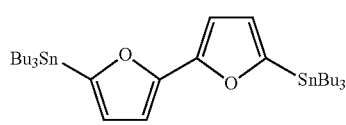

1

2',2-(Tributylstannyl)-2,2'-bifuran (1). A solution of n-BuLi (16 mL, 2.5M in hexanes, 40 mmol) was added dropwise to a solution of bifuran (2.2 g, 16.5 mmol) in dry tetrahydrofuran (THF, 50 mL) at −78° C. under $N_2$. The reaction mixture was allowed to reach to room temperature and stirred for 1 h. The resulting white suspension was cooled to −78° C., $Bu_3SnCl$ (11 mL, 40 mmol) was added dropwise and the reaction mixture was allowed to reach room temperature and stirred for 2 h. The mixture was quenched with water, extracted with hexane, dried ($MgSO_4$), and evaporated. Flash chromatography on a basified ($NEt_3$) silica, using hexane as eluent gave 1 (1.6 g, 14% yield) as a colorless oil, and 2 1 (0.5 g, 7% yield) as a colorless oil.

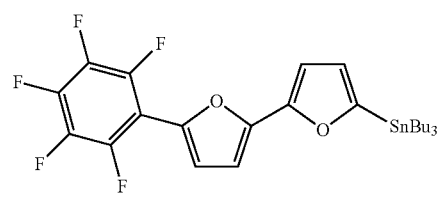

3

DPFB-2F

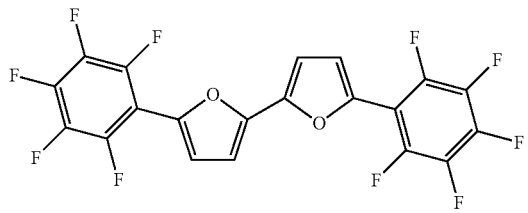

5,5'-bis(perfluorophenyl)-2,2'-bifuran (DPFB-2F) and tributyl(5'-(perfluorophenyl)-[2,2'-bifuran]-5-yl)stannane (3) $Pd(PPh_3)_4$ (10 mg, 0.3 mmol, 10% mol) was added to bromo-pentafluorobenzene (200 mg, 0.8 mmol) and 1 (0.5 g, 0.7 mmol) in dry toluene (20 mL), and the reaction mixture was refluxed under $N_2$ for 4 h. The mixture was then cooled, separated with water/hexane mixture, and the organic fractions were dried ($MgSO_4$) and evaporated. Flash chromatography on a basified ($NEt_3$) silica, using hexane as eluent gave 3 (200 mg, 33% yield) and DPFB-2F (100 mg, 8% yield).

Figure 18:
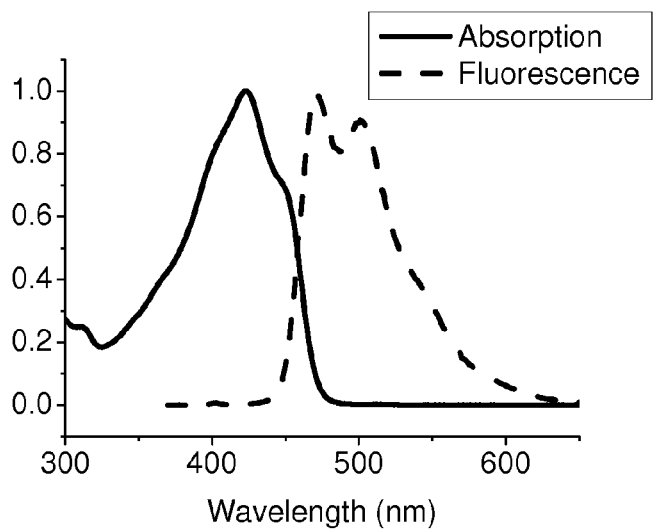
FIG. 18 depicts absorption and fluorescence spectra of DPFB-6F in dioxane.

5,5''''-bis(perfluorophenyl)-2,2':5',2'':5'',2''':5''',2'''':5'''',2''''''-sexifuran (DPFB-6F) $Pd(PPh_3)_4$ (140 mg, 0.12 mmol, 10% mol) was added to 2,2'-(dibromo)bifuran (170 mg, 0.6 mmol) and 3 (700 mg, 2.80 mmol) in dry toluene (100 mL), and the reaction mixture was refluxed under $N_2$ for 3 h. The mixture was then cooled, concentrated to approximately 20 mL, the residue was collected by filtration, washed with hexane and aceton sublimed under reduced pressure (10-2 mbar) at 260° C. to give 150 mg of DPFB-6F (17% yield) as a bright yellow powder. HRMS (FD): m/z calcd for $C_{36}H_{12}F_{10}O_6$: 730.0474. Found 730.0485. UV ABS and Fluorescence of DPFB-6F is presented in FIG. 18.

What is claimed is:

1. A process for the preparation of oligofuran of formula III(n+2m) comprising reacting a compound represented by the structure of formula I:

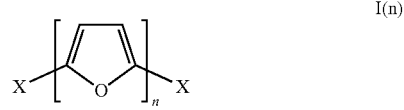

I(n)

with 2- (tributyltin)-oligofuran of formula II:

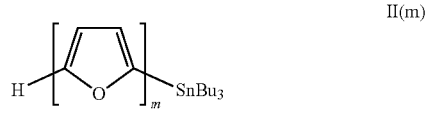

II(m)

to yield oligofuran of formula III(n+2m):

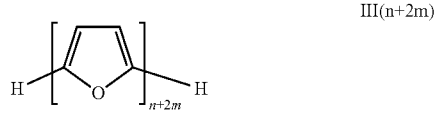

III(n+2m)

wherein X is Br or I;
m is an integer between 1-20; and
n is an integer between 1-20.

2. The process of claim 1, wherein said m is an integer between 1-3; and said n is an integer between 1-3.

3. The process of claim 1, wherein said m is 1 and said n is 2.

4. The process of claim 1, wherein said m is 2 and said n is 1.

5. The process of claim 1, wherein said m is 2 and said n is 2.

6. The process of claim 1, wherein said m is 2 and said n is 3.

DPFB-6F

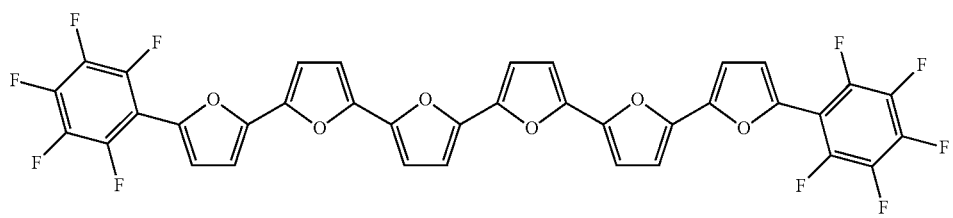

7. The process of claim 1, wherein said m is 3 and said n is 2.

8. The process of claim 1, wherein said m is 3 and said n is 3.

9. The process according to claim 1, wherein said oligofuran of formula I(n) reacts with said oligofuran of formula II(m) in the presence of tetrakis (triphenylphosphine) Palladium [Pd(PPh$_3$)$_4$].

10. The process according to claim 1, wherein said oligofuran of formula I(n) is prepared by bromination of the corresponding oligofuran of formula III(n):

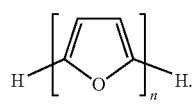

IIIn

11. The process of claim 10, wherein said bromination is in the presence of N-bromosuccinimide (NBS).

12. The process of claim 1, wherein said oligofuran of formula II(m) is prepared by reacting the corresponding oligofuran of formula III(m):

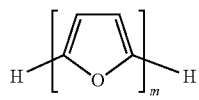

III(m)

with n-butyllithium (n-BuLi) followed by addition of tributyltin chloride (Bu$_3$SnCl).

13. An oligofuran of formula III(n+2m) prepared according to a process comprising reacting a compound represented by the structure of formula I:

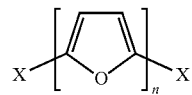

I(n)

with 2-(tributyltin)-oligofuran of formula II:

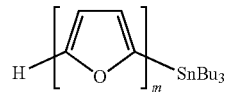

II(m)

to yield oligofuran of formula III(n+2m):

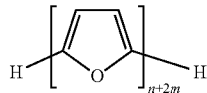

III(n+2m)

wherein X is Br or I;
m is an integer between 1-20; and
n is an integer between 1-20, wherein [n+2m] is not 3 or 4.

14. The oligofuran of claim 13, wherein said oligofuran is fluorescent.

15. A fluorescent marker comprising the oligofuran of claim 13.

16. A field effect transistor device comprising the oligofuran of claim 13.

17. A light emitting transistor device comprising the oligofuran of claim 13.

* * * * *